United States Patent
Nakamura

(10) Patent No.: US 12,061,184 B2
(45) Date of Patent: Aug. 13, 2024

(54) GAS CONSTITUENT MEASURING APPARATUS

(71) Applicant: Panasonic Intellectual Property Management Co., Ltd., Osaka (JP)

(72) Inventor: Kunihiko Nakamura, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 312 days.

(21) Appl. No.: 17/006,756

(22) Filed: Aug. 28, 2020

(65) Prior Publication Data

US 2020/0393443 A1 Dec. 17, 2020

Related U.S. Application Data

(63) Continuation of application No. PCT/JP2019/001599, filed on Jan. 21, 2019.

(30) Foreign Application Priority Data

Mar. 30, 2018 (JP) .................. 2018-068464
Dec. 14, 2018 (JP) .................. 2018-234600

(51) Int. Cl.
  *G01N 33/497* (2006.01)
  *G01F 1/36* (2006.01)
  (Continued)

(52) U.S. Cl.
  CPC ............ *G01N 33/497* (2013.01); *G01F 1/36* (2013.01); *G01N 1/24* (2013.01); *G01N 1/28* (2013.01);
  (Continued)

(58) Field of Classification Search
  CPC ............ G01N 33/497; G01N 33/4972; G01N 2033/4975; G01N 2033/4977; G01N 2001/2276; G01N 33/0016
  See application file for complete search history.

(56) References Cited

U.S. PATENT DOCUMENTS 5,020,628 A * 6/1991 Bigliardi ............ G01N 33/4972
                                              340/576
5,418,131 A * 5/1995 Butts ....................... C12M 41/14
                                              422/123

(Continued)

FOREIGN PATENT DOCUMENTS

JP    03277961 A  * 12/1991
JP    5-099868       4/1993
(Continued)

OTHER PUBLICATIONS

Espacenet Machine Translation of JP-H-03277961 A Which Originally Published on Dec. 9, 1991. (Year: 1991).*

(Continued)

*Primary Examiner* — Alexander A Mercado
(74) *Attorney, Agent, or Firm* — Rimon P.C.

(57) ABSTRACT

A gas constituent measuring apparatus includes a cell that draws in a first gas to be measured, gas sensors that respond to one or more types of constituent gases in the cell, a regulator that controls humidity in the cell, a pump, a humidity sensor that detects the humidity in the cell, and an integrated circuit. The integrated circuit controls the regulator and pump on the basis of a detection result of the humidity sensor so that the humidity is within a predetermined range before the first gas is drawn into the cell or after the first gas is discharged from the cell, acquires first response values from the gas sensors with humidity being controlled, acquires second response values from the gas sensors with the first gas being in the cell, and determines (Continued)

concentrations of the one or more types of constituent gases from the first and second response values.

11 Claims, 14 Drawing Sheets

(51) Int. Cl.
*G01N 1/22* (2006.01)
*G01N 1/24* (2006.01)
*G01N 1/28* (2006.01)
*G01N 27/02* (2006.01)

(52) U.S. Cl.
CPC ..... *G01N 27/02* (2013.01); *G01N 2001/2244* (2013.01)

(56) References Cited

U.S. PATENT DOCUMENTS

| | | | | |
|---|---|---|---|---|
| 5,789,659 | A * | 8/1998 | Williams | G01N 33/007 73/31.06 |
| 5,795,787 | A * | 8/1998 | Silkoff | G01N 33/497 128/203.14 |
| 6,488,635 | B1 * | 12/2002 | Mottram | A61B 5/083 119/14.01 |
| 6,595,037 | B2 * | 7/2003 | McGinley | G01N 33/0001 73/23.3 |
| 6,723,056 | B1 * | 4/2004 | Alving | G01N 33/497 600/543 |
| 7,058,518 | B2 * | 6/2006 | Shoji | G01N 27/18 702/24 |
| 7,385,681 | B2 * | 6/2008 | Ninomiya | F23N 5/24 356/5.01 |
| 8,683,845 | B2 * | 4/2014 | Fleischer | G01N 27/4143 73/23.21 |
| 8,741,120 | B2 * | 6/2014 | Chapples | G01N 27/4067 236/44 R |
| 9,347,875 | B2 * | 5/2016 | Miyai | G01N 21/3504 |
| 9,366,664 | B2 * | 6/2016 | Anglin, Jr. | G01N 33/497 |
| 9,901,288 | B2 * | 2/2018 | Gollar | A61B 5/097 |
| 9,931,055 | B2 * | 4/2018 | Forzani | A61B 5/082 |
| 10,130,284 | B2 * | 11/2018 | Johnson | G01N 33/497 |
| 10,278,617 | B1 * | 5/2019 | Satterfield | G01N 33/497 |
| 10,359,382 | B2 * | 7/2019 | Moss | G01N 33/0032 |
| 10,436,737 | B2 * | 10/2019 | Sussner | G01N 29/022 |
| 10,712,306 | B2 * | 7/2020 | Umasankar | G01N 33/64 |
| 10,877,008 | B2 * | 12/2020 | DeVries | G01N 33/0006 |
| 10,883,967 | B2 * | 1/2021 | Hattori | G01N 29/036 |
| 11,162,928 | B2 * | 11/2021 | Goel | G01N 33/006 |
| 11,187,711 | B1 * | 11/2021 | Lynn | B01L 7/52 |
| 11,243,198 | B2 * | 2/2022 | Lin | G01N 33/0006 |
| 2001/0027678 | A1 | 10/2001 | Mottram et al. | |
| 2003/0010653 | A1 * | 1/2003 | Ando | G01N 33/0037 205/781 |
| 2005/0116160 | A1 * | 6/2005 | Guevremont | G01N 21/3504 250/282 |

FOREIGN PATENT DOCUMENTS

JP 9-243537 A 9/1997
JP 2005-257373 9/2005

OTHER PUBLICATIONS

Espacenet Machine Translation of JP-H-09243537 A Which Originally Published on Sep. 19, 1997. (Year: 1997).*
Espacenet Machine Translation of JP 2013079832 A Which Originally Published on May 2, 2013. (Year: 2013).*
International Search Report of PCT application No. PCT/JP2019/001599 dated Mar. 5, 2019.
K. Nakamura et al., "Determination of Low Concentration of Multi-target Gas Species Exhaled with the Breath", ECS Transactions, 75(16), 2016, pp. 83-90.
Koichi Suematsu et al., "Antimony-Doped Tin Dioxide Gas Sensors Exhibiting High Stability in the Sensitivity to Humidity Changes", ACS Sensors, 1(7), Jun. 10, 2016, pp. 913-920.

* cited by examiner

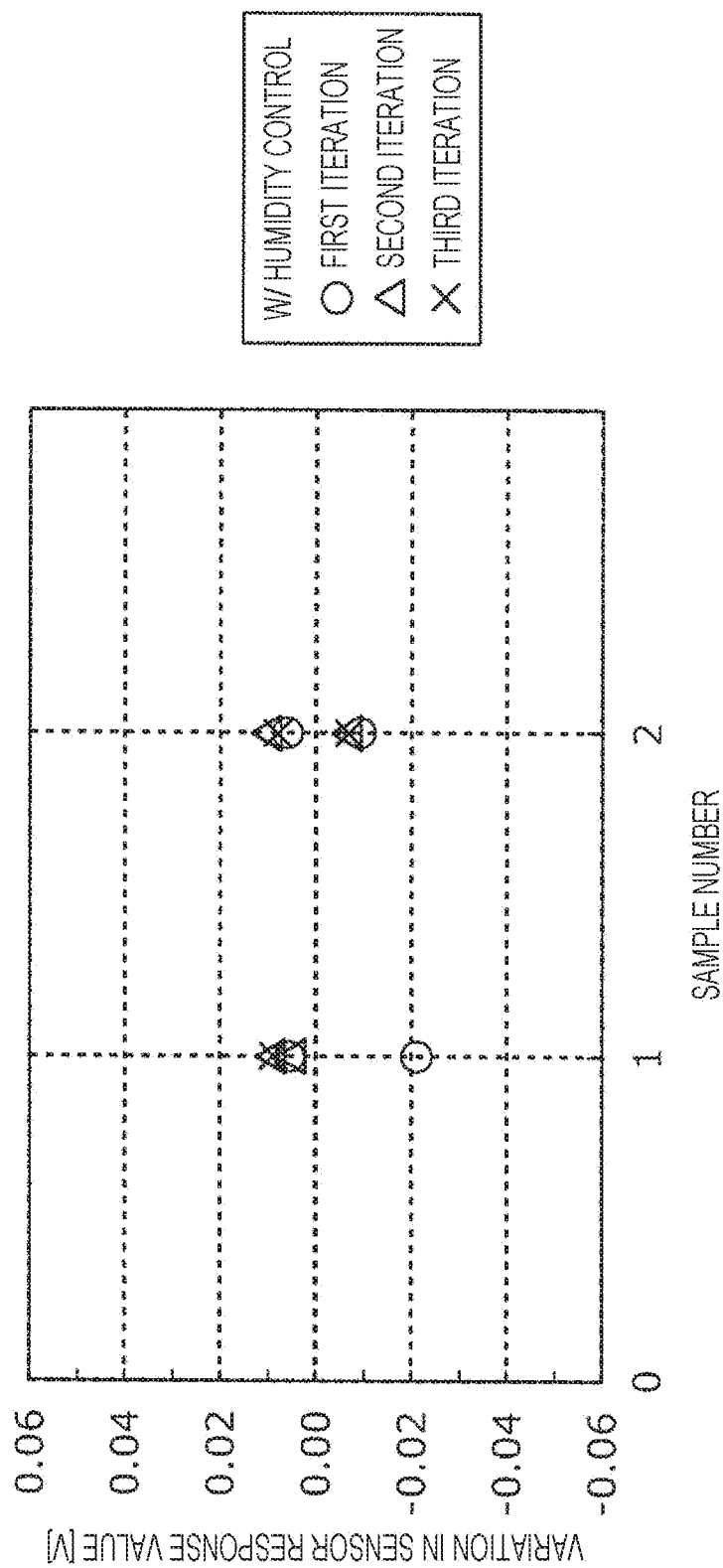

FIG. 14

$$\begin{bmatrix} S_A = f_1(x, y, z) \\ S_B = f_2(x, y, z) \\ S_C = f_3(x, y, z) \end{bmatrix}$$

⇓ INVERSE FUNCTION $$\begin{bmatrix} x = f_1^{-1}(S_A, S_B, S_C) \\ y = f_2^{-1}(S_A, S_B, S_C) \\ z = f_3^{-1}(S_A, S_B, S_C) \end{bmatrix}$$

GAS CONSTITUENT MEASURING APPARATUS

BACKGROUND

1. Technical Field

The present disclosure relates to a gas constituent measuring apparatus that measures the concentration of a constituent gas contained in a gas to be measured by using a gas sensor.

2. Description of the Related Art

Exhaled air and skin gas contain rich metabolic information and can be collected in a minimally invasive manner. Apparatuses that measure the concentrations of constituent gases contained in these gases can be widely used in hospitals, workplaces, homes and the like for health and safety purposes (refer to, for example, Japanese Unexamined Patent Application Publication No. 2005-257373; K. Nakamura, T. Hosokawa, Y. Morita, M. Nishitani, and Y. Sadaoka, Determination of Low Concentration of Multi-Target Gas Species Exhaled with the Breath, ECS Transactions, 2016, 75(16) 83-90; and K. Suematsu, M. Sasaki, N. Ma, M. Yuasa, and K. Shimanoe, "Antimony-Doped Tin Dioxide Gas Sensors Exhibiting High Stability in the Sensitivity to Humidity Changes", ACS Sens., 2016, 1(7), 913-920). The concentration of the constituent gas contained in these gases can be measured by, for example, separating the constituent gas from exhaled air or skin gas by gas chromatography.

SUMMARY

One non-limiting and exemplary embodiment provides a gas constituent measuring apparatus capable of easily and highly accurately measuring the concentration of a constituent gas contained in a gas to be measured.

In one general aspect, the techniques disclosed here feature a gas constituent measuring apparatus including a cell that draws in a first gas to be measured, a gas sensor that responds to one or more types of constituent gases present in the cell, a regulator that controls humidity in the cell, a humidity sensor that detects the humidity in the cell, and an integrated circuit. The integrated circuit controls the regulator on the basis of a result of detection of the humidity sensor so that the humidity in the cell is within a predetermined range before the first gas is drawn into the cell or after the first gas is discharged from the cell. The integrated circuit acquires a first response value output from the gas sensor for the inside of the cell having a humidity controlled through the control performed on the regulator. The integrated circuit acquires a second response value output from the gas sensor for the first gas drawn into the cell after the first gas is drawn into the cell, and the integrated circuit determines the concentration of each of the one or more types of constituent gases on the basis of the first response value and the second response value.

According to the gas constituent measuring apparatus according to an embodiment of the present disclosure, a gas constituent measuring apparatus capable of easily and highly accurately measuring the concentration of a constituent gas contained in the gas to be measured is provided.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 12E is a graph illustrating an example of the repetitive reproducibility of a response value output from a gas sensor in accordance with the presence/absence of humidity control (a graph in which the variation in repetitive reproducibility in FIG. 12C is enlarged for sample numbers 1 and 2 at low concentration condition);

FIG. 14 is a diagram illustrating an example of the correspondence between gas concentrations and the response value of a gas sensor.

DETAILED DESCRIPTION

Figure 1:
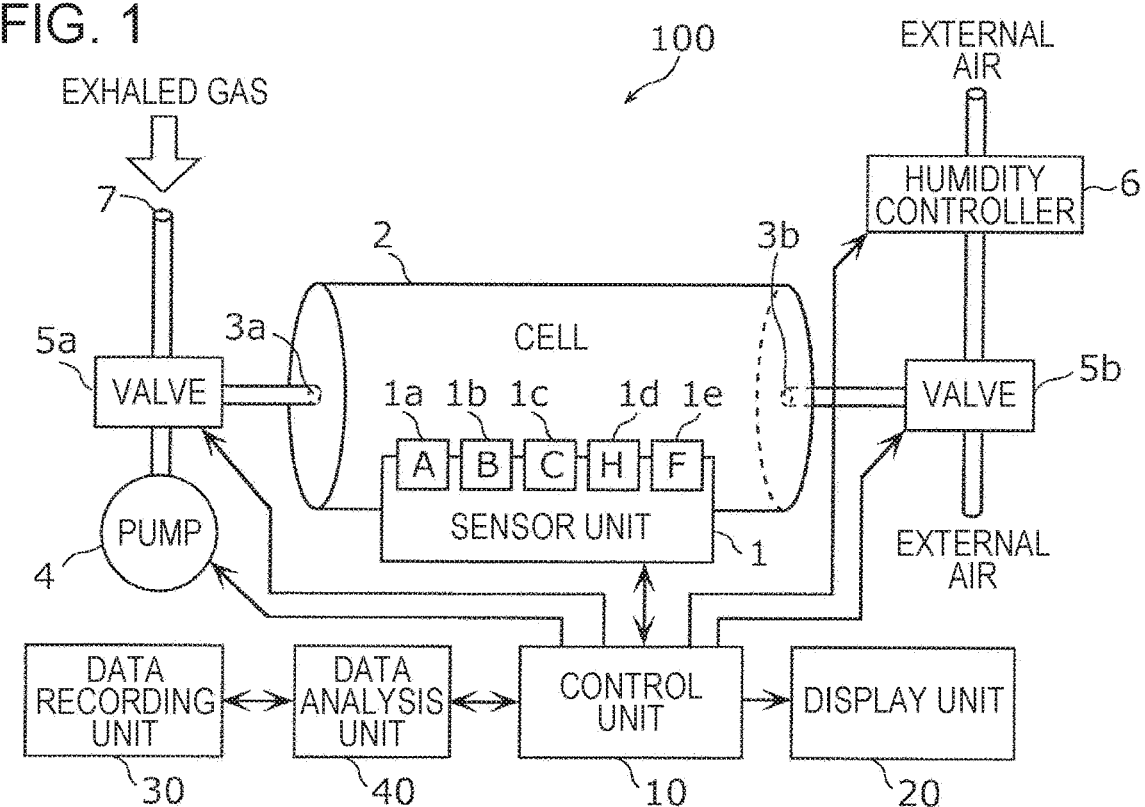
FIG. 1 is a block diagram illustrating an example of the functional configuration of an exhaled air constituent measuring apparatus according to a first embodiment.

Underlying Knowledge Forming Basis of the Present Disclosure

As described above, apparatuses for gas chromatography are too expensive and too complicated in configuration and control for being widely used as a gas constituent measuring apparatus for households and individuals. In contrast, a semiconductor gas sensor is inexpensive and simple in configuration and control, while the accuracy of gas concentration measurement is not always sufficient.

A semiconductor gas sensor is a gas sensor having a metal oxide as a main material. Semiconductor gas sensors have recently been mass-produced inexpensively and have been used as an alcohol detector for drivers, an indoor environment monitor, and a gas leak alarm for city gas.

Among gas constituent measuring apparatuses, a semiconductor gas sensor is designed to measure a variety of types of gases. Examples of a constituent gas in the exhaled gas that is supposed to be measured include acetone, which is a product of fat metabolism in the body, alcohols caused by drinking, volatile sulfide compounds that cause bad breath, and hydrogen produced by anaerobic bacteria in the intestines.

The response value of the semiconductor gas sensor has a humidity dependence, and this humidity dependence has to be taken into account in order to measure the concentration of a constituent gas with high accuracy.

The response value of a semiconductor gas sensor is described below in more detail.

In general, a semiconductor gas sensor (hereinafter also simply referred to as a "gas sensor") responds with a sensitivity unique to the type of gas among a plurality of types of gases. That is, the response value (for example, an output voltage) of the gas sensor for a mixture gas of the plurality of constituent gases is expressed as a function of the concentrations of the plurality of constituent gases. Note that the presence of the humidity dependence of the response value of the gas sensor means that the response value of the gas sensor is expressed as a function of the concentration of water vapor in addition to the concentrations of the constituent gases.

FIG. 14 is a diagram illustrating an example of the correspondence between the gas concentration and the response value of the gas sensor. In the example illustrated in FIG. 14, the concentrations of the component gases X, Y, and Z are denoted as x, y, and z, respectively. In addition, response values $S_A$, $S_B$, and $S_C$ of the gas sensors A, B and C are denoted as functions $f_1(x, y, z)$, $f_2(x, y, z)$, and $f_3(x, y, z)$, respectively.

The functions $f_1$, $f_2$, and $f_3$ are identified by, for example, measuring a plurality of sample gases having known concentrations x, y, and z with the gas sensors A, B, and C, respectively, and solving a simultaneous equation by using the response values $S_A$, $S_B$, and $S_C$ of the gas sensors A, B, and C, respectively, and the known concentrations x, y, and z. Furthermore, inverse functions $f_1^{-1}$, $f_2^{-1}$, $f_3^{-1}$ of the functions $f_1$, $f_2$, and $f_3$, respectively, are identified from the functions $f_1$, $f_2$, $f_3$.

The concentrations x, y, z of the constituent gases X, Y, Z contained in the exhaled air to be measured are calculated as the inverse function values $f_1^{-1}(S_A, S_B, S_C)$, $f_2^{-1}(S_A, S_B, S_C)$, and $f_3^{-1}(S_A, S_B, S_C)$ of the response values $S_A$, $S_B$, and $S_C$ of the gas sensors A, B, and C for the exhaled air, respectively.

The expression form of the function and the inverse function is not limited to a particular form. The function and the inverse function may be expressed in any form, such as a mathematical expression, a numerical table, or a neural net.

From the understanding in FIG. 14, by considering water vapor as one of the constituent gases to be measured and processing a variate representing the concentration of water vapor (that is, the humidity of the exhaled air), the concentrations of the plurality of constituent gases including water vapor can be accurately measured.

As described above, there are various types of constituent gases in the exhaled air that are supposed to be measured by the gas constituent measuring apparatus. By measuring the concentrations of more constituent gases and examining the state of health of a user from the measurement results in a multifaceted manner, a determination result with a higher added value can be obtained.

However, measuring the concentrations of more constituent gas based on the idea described in FIG. 14 increases the number of variates of the functions. If the number of variates of the functions is increased, the number of samples required for identifying the functions increases, and the time required for measuring the sample gas increases. Furthermore, the amount of calculation for identifying the function and the inverse function also increases. Therefore, to reduce the cost in terms of time and amount of calculation and to obtain a gas constituent measuring apparatus that is inexpensive and that has simple configuration and control, it is desirable that the number of variates of the functions be reduced to minimum.

Therefore, as a result of earnest studies, the present inventor has conceived an idea of a gas constituent measuring apparatus capable of highly accurately measuring the concentration of a constituent gas contained in a gas to be measured by using a gas sensor that does not rely on gas chromatography.

According to an aspect of the present disclosure, a gas constituent measuring apparatus includes a cell that draws in a first gas to be measured, a gas sensor that responds to one or more types of constituent gases present in the cell, a regulator that controls humidity in the cell, a humidity sensor that detects the humidity in the cell, and an integrated circuit. The integrated circuit controls the regulator on the basis of a result of detection of the humidity sensor so that the humidity in the cell is within a predetermined range before the first gas is drawn into the cell or after the first gas is discharged from the cell. The integrated circuit acquires a first response value output from the gas sensor for the inside of the cell having a humidity controlled through the control performed on the regulator. The integrated circuit acquires a second response value output from the gas sensor for the first gas drawn into the cell after the first gas is drawn into the cell, and the integrated circuit determines the concentration of each of the one or more types of constituent gases on the basis of the first response value and the second response value.

In this manner, the concentration of the constituent gas contained in the first gas is determined from the first response value obtained when the humidity in the cell is within the predetermined range and the second response value obtained when the first gas to be measured is introduced into the cell. Since the concentration of the constituent gas contained in the first gas can be determined by using, as a reference, the first response value obtained when the concentration of water vapor is constant. Consequently, even when the gas sensor responds to water vapor, the influence of the water vapor is constant. Thus, a determination result with little humidity dependence is obtained. As a result, a gas constituent measuring apparatus capable of measuring the concentration of a constituent gas contained in the first gas with high accuracy in a simple manner can be achieved while using a gas sensor that does not rely on gas chromatography.

In addition, for example, the regulator may include at least one of a humidifier and a dehumidifier and a pump that introduces, into the cell, a second gas humidified by the humidifier or dehumidified by the dehumidifier. The integrated circuit may control the introduction of the second gas into the cell so that the humidity in the cell is within the predetermined range.

In this manner, by using the humidified or dehumidified second gas, the humidity in the cell can be efficiently controlled so as to be within the predetermined range.

In addition, for example, the humidifier or the dehumidifier may draw in air outside the gas constituent measuring apparatus and humidify or dehumidify the drawn air as the second gas.

In this manner, the second gas can be easily generated from the external air.

In addition, for example, the regulator may further include a valve that opens and closes the flow of the second gas introduced into the cell.

In addition, for example, the cell may have a plurality of openings including a first opening and a second opening that differs from the first opening. The first gas may be drawn into the cell through the first opening, and the second gas may be introduced into the cell through the second opening.

In this manner, an introduction path of the first gas and an introduction path of the second gas can be separated from each other and, thus, the first gas and the second gas can be prevented from being mixed with each other. As a result, the concentration of the constituent gas contained in the first gas can be measured with higher accuracy.

In addition, for example, the gas constituent measuring apparatus may further include a first presentation device. The integrated circuit may cause the first presentation device to give a predetermined presentation to a user if the humidity inside the cell reaches a value within the predetermined range due to the control performed on the regulator.

In this manner, the user can start drawing of the first gas on the basis of the presentation given by the first presenting device. As a result, the operability of the gas constituent measuring apparatus is improved.

In addition, for example, the gas constituent measuring apparatus may further include a flow rate detector that detects the flow rate of the first gas drawn into the cell and a second presentation device. The integrated circuit may cause the second presentation device to give, to a user, a presentation regarding a result of detection made by the flow rate detector so that the first gas is drawn into the cell at predetermined flow rate for a predetermined period of time.

In this manner, the user can control the drawing of the first gas on the basis of the presentation given by the second presentation device. As a result, the concentration of a constituent gas contained in the first gas can be measured with higher accuracy.

In addition, for example, the gas constituent measuring apparatus may further include a recording medium. If training gas containing one or more constituent gases whose concentrations are already known is drawn into the cell, the integrated circuit may acquire a third response value output from the gas sensor for the training gas drawn into the cell. The integrated circuit may control the regulator on the basis of the result of detection output from the humidity sensor so that the humidity in the cell is within a predetermined range before the training gas is drawn into the cell or after the training gas is discharged from the cell. The integrated circuit may acquire a fourth response value output from the gas sensor for the inside of the cell having a humidity controlled through the control performed on the regulator. The integrated circuit may record, on the recording medium, information regarding a correspondence between the third response value, the fourth response value and the known concentration, and the integrated circuit may make the determination on the basis of the first response value, the second response value, and the information.

In this manner, the information for determining the concentration of a constituent gas of the first gas is obtained by measuring the training gas with the same gas sensor that measures the first gas. As a result, the concentration of a constituent gas contained in the first gas can be measured with higher accuracy.

It should be noted that general or specific embodiments may be implemented as a system, a method, an integrated circuit, a computer program, a computer-readable storage medium, such as a compact disc-read only memory (CD-ROM), or any selective combination thereof.

A gas constituent measuring apparatus according to an aspect of the present disclosure is described in detail below with reference to the accompanying drawings.

It should be noted that each of the embodiments described below is a particular example of the present disclosure. A value, a shape, a material, a constituent element, the positions and the connection form of the constituent elements, steps, and the sequence of steps described in the embodiments are only examples and shall not be construed as limiting the scope of the present disclosure. In addition, among the constituent elements in the embodiments described below, the constituent element that does not appear in an independent claim, which has the broadest scope, is described as an optional constituent element.

First Embodiment

A gas constituent measuring apparatus according to the first embodiment is described below with reference to an example of an exhaled air constituent measuring apparatus.

FIG. 1 is a block diagram illustrating an example of the functional configuration of the exhaled air constituent measuring apparatus according to the first embodiment. As illustrated in FIG. 1, the exhaled air constituent measuring apparatus 100 includes a sensor unit 1, a cell 2, air supply and exhaust openings 3a and 3b, a pump 4, valves 5a and 5b, a humidity controller 6, a gas inlet 7, and a control unit 10, a display unit 20, a data recording unit 30, and a data analysis unit 40. The sensor unit 1 includes gas sensors 1a, 1b, and 1c, a humidity sensor 1d, and a flow rate detector 1e.

Each of the gas sensors 1a, 1b, and 1c is a gas sensor that responds to a gas A, a gas B, and a gas C contained in the exhaled air. The gas A, gas B, and gas C are, for example, acetone, which is a product of fat metabolism in the body, alcohols, products of alcohol drinking, volatile sulfide compounds that cause bad breath, hydrogen derived from anaerobic bacteria in the intestine, and carbon monoxide which serves as an asthma marker.

The gas sensor 1a responds not only to the gas A but also to the gas B and the gas C. The gas sensor 1a is further influenced by humidity (the concentration of water vapor). Similarly, the gas sensors 1b and 1c respond not only to the gases B and C, respectively, but also to other gases. The gas sensors 1b and 1c are further influenced by humidity (the concentration of water vapor).

The cell 2 is a container that draws in and holds the exhaled air. In the example illustrated in FIG. 1, the cell 2 has a cylindrical shape. The air supply and exhaust openings 3a and 3b are provided at either end of the cell 2. The air supply and exhaust openings 3a and 3b are openings for exchanging gas between the inside and outside of the cell 2. The locations at which the openings are disposed in the cell are not limited to particular positions. However, to efficiently ventilate the cell, the openings are disposed at either end of the cylindrical cell, as illustrated in FIG. 1. In contrast, to cause the gas sensor disposed in the cell to respond slowly to the supplied gas and obtain, as an output of the sensor, an average concentration which is insensitive to short-term concentration unevenness of the inhaled gas, the air supply opening and the air exhaust opening are not located on a straight line of the gas flow. For example, one of the openings may be disposed on the side surface of the cylindrical cell. In addition, a gas reservoir that is difficult to ventilate may be provided in the cell, and the other may be disposed in the gas reservoir.

The pump 4 and the valve 5a are connected to the air supply and exhaust opening 3a. The humidity controller 6 and the valve 5b are connected to the air supply and exhaust opening 3b.

The humidity controller 6 controls the humidity of the external air introduced into the cell before the exhaled air is drawn in. The pump 4, the valves 5a and 5b, and the humidity controller 6 are examples of regulators that control the humidity in the cell 2.

Note that the humidity controller 6 is not limited to being placed outside the cell 2. For example, the cell 2 may include a miniaturized humidity controller 6 and a pump for discharging the gas having humidity controlled by the humidity controller 6 to the outside of the humidity controller 6. Furthermore, a valve for opening and closing the air supply opening and/or the air exhaust opening of the humidity controller 6 in the cell 2 may be provided. That is, instead of introducing the external air having humidity regulated by the humidity controller 6, the unregulated external air may be introduced and, thereafter, the humidity in the cell 2 may be regulated by the humidity controller 6 disposed inside the cell 2. In this case, the humidity controller 6, the pump, and the valve in the cell 2 correspond to the regulator that controls the humidity in the cell 2.

Figure 2:
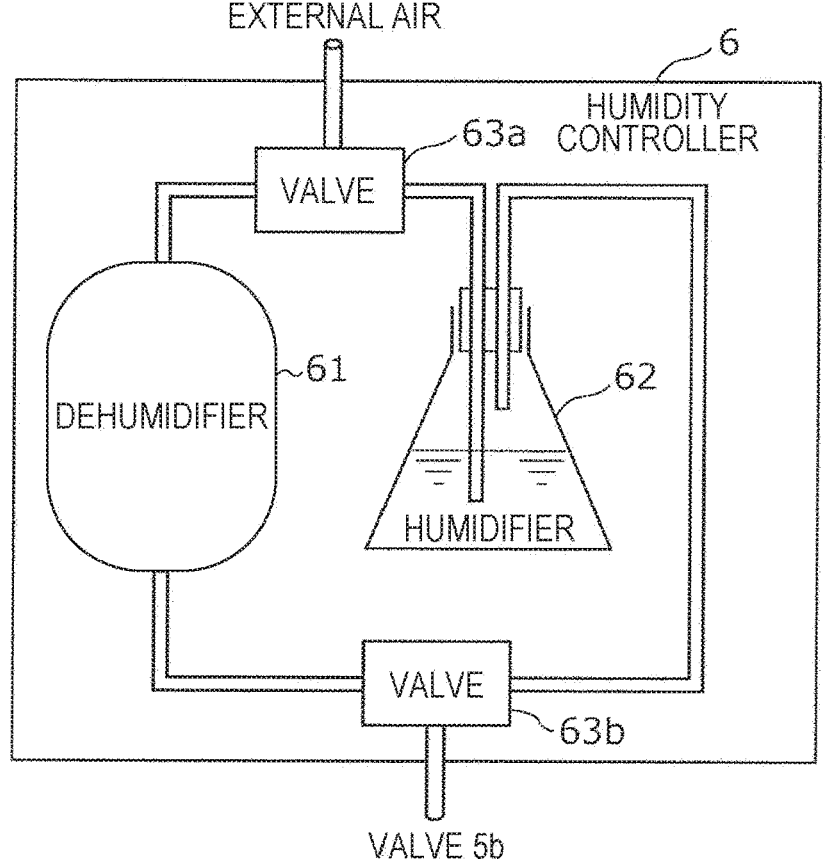
FIG. 2 is a block diagram illustrating the functional configuration of a humidity controller according to the first embodiment.

FIG. 2 is a block diagram illustrating an example of the functional configuration of the humidity controller 6. As illustrated in FIG. 2, the humidity controller 6 includes a dehumidifier 61, a humidifier 62, and valves 63a and 63b.

The dehumidifier 61 is a cylinder containing a desiccant, such as silica gel or molecular sieve.

The humidifier 62 is a water storage container that performs bubbling for humidification.

The valve 63a is, for example, a three-way valve. The valve 63a selectively causes external air to communicate with one of the dehumidifier 61 and the humidifier 62.

The valve 63b is, for example, a three-way valve. The valve 63b selectively causes one of the dehumidifier 61 and the humidifier 62 to communicate with the valve 5b.

According to the humidity controller 6, the external air can be dehumidified or humidified by using one of the dehumidifier 61 and the humidifier 62 selected by the valves 63a and 63b. Note that the humidity controller 6 may have only one of the dehumidifying function and the humidifying function.

Referring back to FIG. 1, the description of the exhaled air constituent measuring apparatus is continued.

A connecting portion between each of the air supply and exhaust openings 3a and 3b and the cell 2 is not limited to a stepped shape as illustrated in FIG. 1. For example, both ends of the cylinder of the cell 2 may be tapered so that the inner diameter of the cylinder is gradually reduced toward the air supply and exhaust openings 3a and 3b. This configuration can reduce retention of gas in the corners of the inside of the cylindrical cell 2 and, thus, reduce the ventilation time for the gas that tends to remain in the corners of the cylinder.

The valves 5a and 5b control the air supply and exhaust at the air supply and exhaust openings 3a and 3b, respectively. The valve 5a is, for example, a three-way valve. The valve 5a selectively enables one of the gas inlet 7 and the pump 4 for introducing the exhaled air to communicate with the air supply and exhaust opening 3a. The valve 5b is, for example, a three-way valve. The valve 5b selectively enables the external air and one end of the humidity controller 6 to communicate with the air supply and exhaust opening 3b. The other end of the humidity controller 6 is open to the external air.

Inside the cell 2, the humidity sensor 1d and the flow rate detector 1e are disposed in addition to the gas sensors 1a, 1b and 1c. The flow rate detector 1e may be a flow meter, for example. The humidity sensor 1d detects the humidity in the cell 2, and the flow rate detector 1e detects the flow rate of the exhaled air drawn into the cell 2.

The control unit 10 controls driving of the variety of sensors, acquisition of measured values, and the gas flow generated by the valves and pumps. That is, the control unit 10 controls a series of sequences from gas introduction to determination of the concentration of a constituent gas. The control unit 10 may be configured by, for example, a personal computer.

The display unit 20 functions as a first presentation unit and displays the information about the humidity in the cell 2. In addition, the display unit 20 functions as a second presentation unit and displays the information about the flow rate into the cell 2. The display unit 20 may be configured by, for example, a display connected to a personal computer.

The data recording unit 30 has a database that stores the response of the sensor unit 1 when a mixture of gases of known concentrations that simulates exhaled air (hereinafter referred to as "artificial exhaled air") is introduced into the cell 2. In addition, the known concentrations and the response of the gas sensor are associated with each other by a mathematical expression, and the coefficients or the like describing the mathematical expression are recorded. The data recording unit 30 may be configured by a recording medium, such as a semiconductor memory.

The data analysis unit 40 determines the unknown concentrations of the gases A, B, and C contained in the exhaled air from the response of the sensor unit 1 to the exhaled air of a user and the mathematical expression stored in the data recording unit 30. The data analysis unit 40 is an example of a determination unit.

Operation Performed by Exhaled Air Constituent Measuring Apparatus

The operation performed by the exhaled air constituent measuring apparatus 100 having the above-described configuration is described below.

Figure 3:
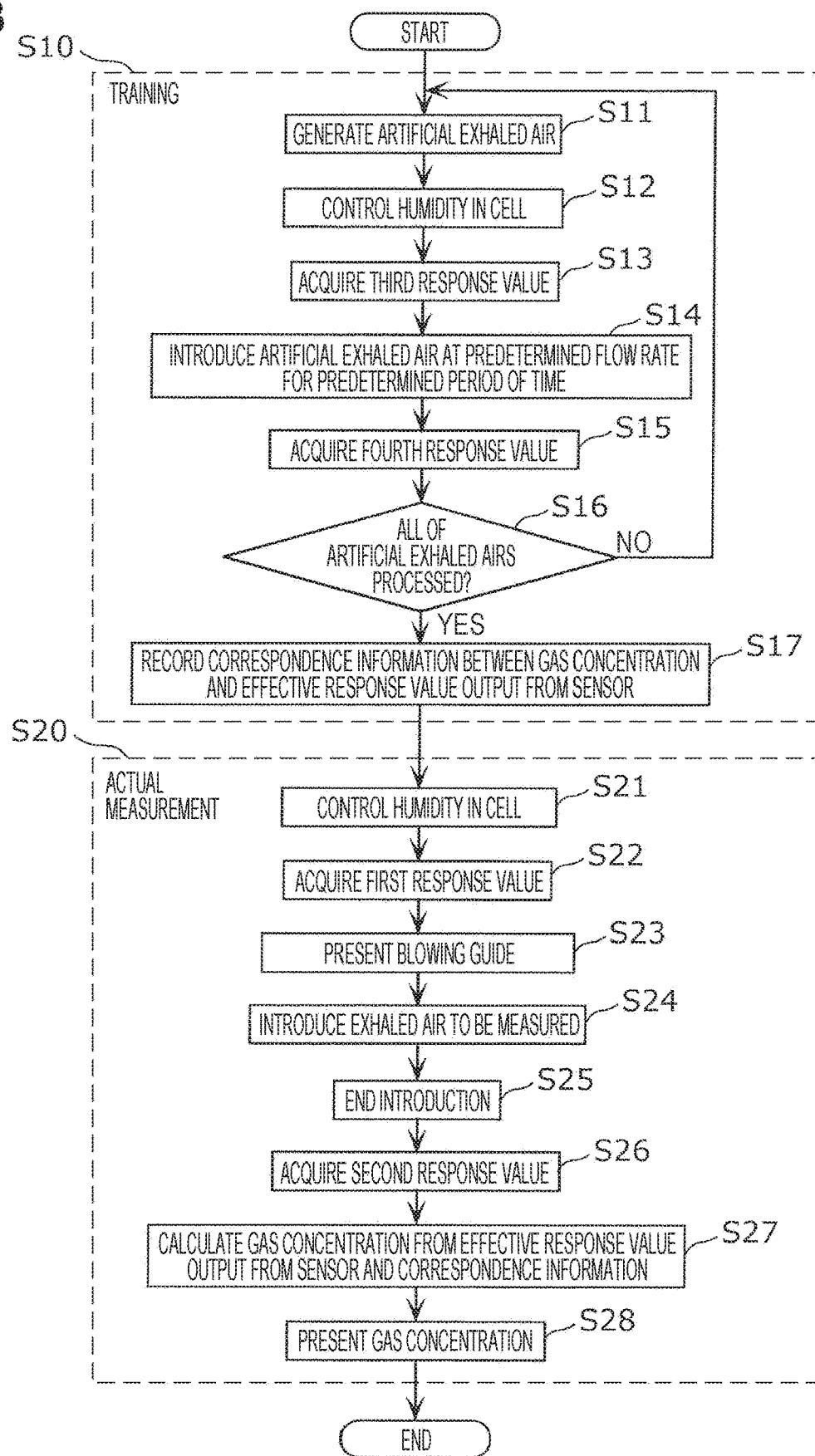
FIG. 3 is a flowchart illustrating an example of the operation performed by the exhaled air constituent measuring apparatus according to the first embodiment.

FIG. 3 is a flowchart illustrating an example of the operation performed by the exhaled air constituent measuring apparatus 100. As illustrated in FIG. 3, the operation performed by the exhaled air constituent measuring apparatus 100 is broadly grouped into a training process (step S10) and an actual measurement process (step S20).

In the training process (step S10), artificial exhaled air for which the concentrations of the constituent gases are known is generated (step S11), and the response value of the gas sensor to the artificial exhaled air is acquired (step S12 to S16). Thereafter, correspondence information regarding the relationship between the response value of the gas sensor and the concentrations of the constituent gases is obtained and recorded (step S17). In this example, the artificial exhaled air is an example of a training gas.

Figure 4:
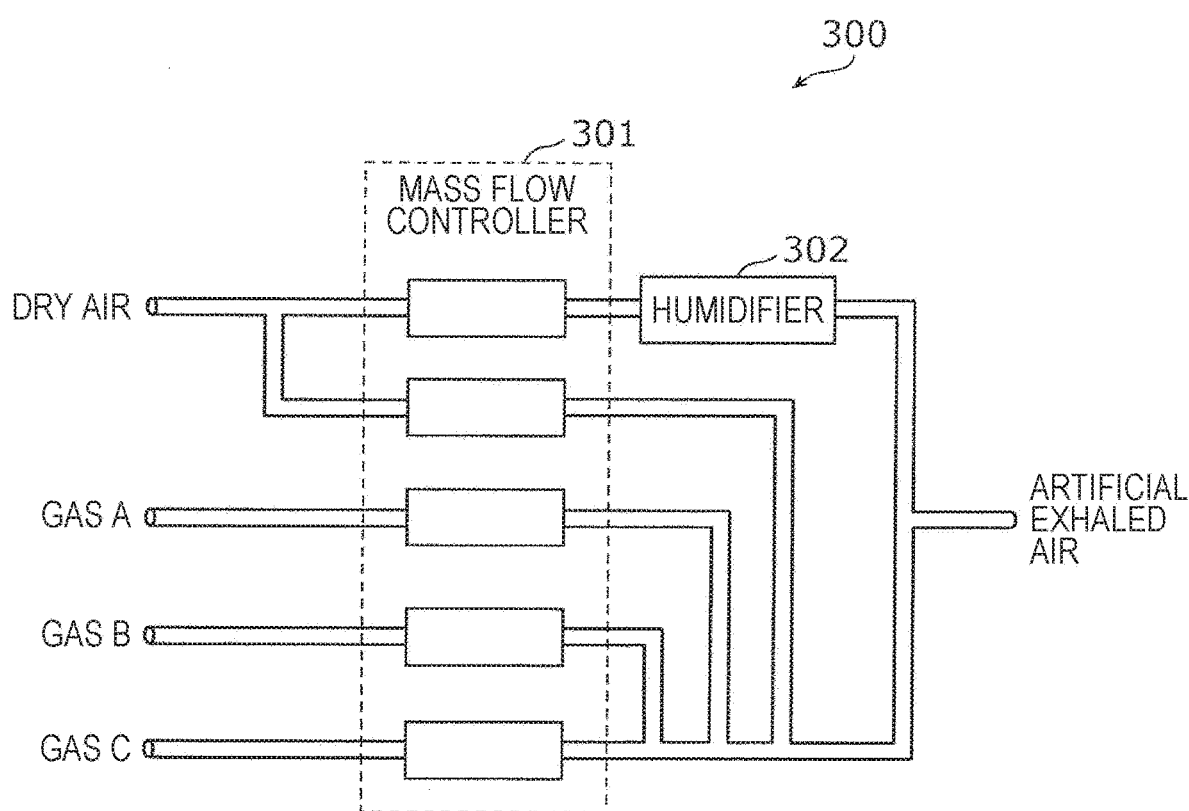
FIG. 4 is a diagram illustrating an example of an artificial exhaled air generating apparatus.

FIG. 4 is a diagram illustrating an example of an artificial exhaled air generating apparatus 300. The artificial exhaled air generating apparatus 300 generates artificial exhaled air by adjusting the flow rates of the gases A, B, and C each having a known concentration and the dry air by using a mass flow controller 301. The dry air is branched into two, one of which is bubbled through water in the humidifier 302 and is turned into humidified air. The humidified air, the other dry air, and the gases A, B, and C are mixed in a flow regulated manner into one, which is supplied to the cell 2 illustrated in FIG. 1 as artificial exhaled air having a humidity that resembles the humidity of the exhaled air. Through the adjustment performed by the mass flow controller 301, a plurality of types of artificial exhaled air are generated, each having a combination of different concentrations of constituent gases to which the gas sensors 1a, 1b, 1c respond.

Referring back to FIG. 3, the humidity in the cell 2 is controlled before the artificial exhaled air is supplied to the cell 2 (step S12).

In step S12, the control unit 10 drives the pump 4 and controls the opening direction of the valve 5a so that the pump 4 can suck the gas in the cell 2. In addition, the control unit 10 controls the opening direction of the valve 5b so that the external air can be drawn into the cell 2 without passing through the humidity controller 6. In this manner, the inside of the cell 2 is ventilated with the external air. This control is necessary to discharge the constituent gases of the exhaled air and the water vapor remaining in the cell 2.

Subsequently, the control unit 10 controls the opening direction of the valve 5b so that the external air can be drawn into the cell 2 via the humidity controller 6. In this manner, the constituent gas of the exhaled air remaining in the cell 2 is further discharged to facilitate dehumidification. The foregoing ventilation which is performed without passing through the humidity controller 6 can be skipped. However, by performing ventilation without using the humidity controller 6 before ventilation using the humidity controller 6, the dehumidification time can be reduced. In this manner, the load imposed on the desiccant can be reduced, and the frequency of exchanging the desiccant can be reduced.

Through step S12, the humidity in the cell 2 can be controlled to a predetermined constant humidity. The constant humidity may be relative humidity or absolute humidity. Furthermore, the constant humidity may be humidity within a predetermined range.

A detailed procedure for controlling the humidity in the cell 2 by dehumidification performed in step S12 is described below.

Figure 5:
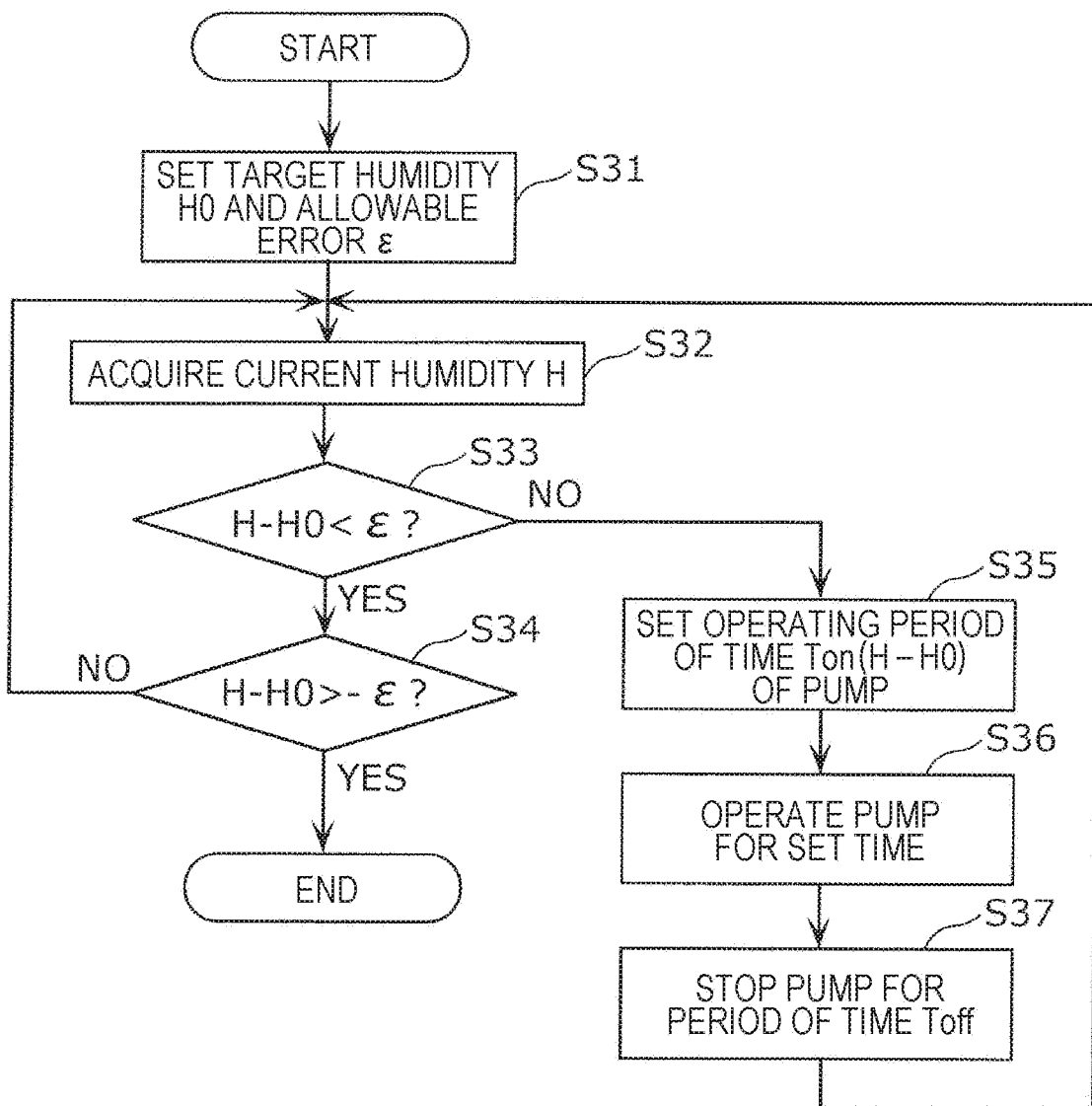
FIG. 5 is a flowchart illustrating an example of a humidity control process according to the first embodiment.

FIG. 5 is a flowchart illustrating an example of a humidity control process by dehumidification.

In the humidity control process by dehumidification, the control unit 10 sets a target humidity H0 and its allowable error ε (>0) first (step S31). For example, if the target humidity H0 is 10% RH and the allowable error ε is 0.5% RH, the humidity in the cell 2 is adjusted within the range of 10±0.5% RH.

The humidity H in the cell 2 is measured by the humidity sensor 1d (step S32).

If a difference H−H0 between the measured humidity H and the target humidity H is less than the allowable error ε (YES in step S33) and is greater than the negative value −ε of the allowable error (YES in step S34), the control unit 10 ends the humidity control process.

However, if H−H0≥ε (NO in step S33), dehumidification is needed. Accordingly, the control unit 10 sets the operating time Ton of the pump 4 (step S35) and operates the pump 4 for the set period of time Ton (step S36). At this time, the opening directions of the valves 5b and 63b are controlled such that the air supply and exhaust opening 3b and the dehumidifier 61 are connected to each other. In addition, the opening direction of the valve 5a is controlled such that the air supply and exhaust opening 3a is connected to the pump 4. As a result, during the time Ton, the external air dehumidified by the dehumidifier 61 is introduced into the cell 2 and, thus, the humidity in the cell 2 decreases.

The control unit 10 stops the pump 4 after the time Ton elapses. Thereafter, the control unit 10 lets the gas in the cell 2 sit for a predetermined time Toff (step S37). After that, the control unit 10 acquires the humidity H again and compares H−H0 with the allowable value ε.

If dehumidification is still insufficient, the same routine from step S32 to step S37 is repeated. At this time, the control unit 10 determines the drive time Ton of the pump on the basis of the value of H−H0. Simply, Ton may be a value obtained by multiplying the value of H−H0 by a proportional coefficient.

Figure 6:
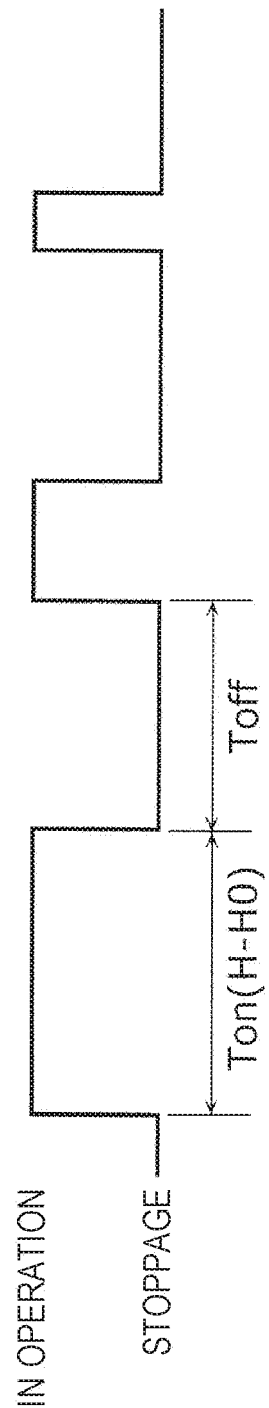
FIG. 6 is a sequence chart illustrating an example of the operation status of a pump according to the first embodiment.

FIG. 6 is a sequence chart illustrating an example of the operation status of the pump 4. The driving time of the pump 4 decreases as the humidity H approaches the target humidity H0. Eventually, the expression |H−H0|<ε is satisfied. At this time, the humidity control process ends.

Note that in the above-described process, the pump 4 is driven within the period of time Ton. However, even if the pump 4 is not driven, the humidity inside the cell 2 decreases as long as the air inside the cell 2 communicates with the dehumidifier 61. If the pump 4 is not driven, it takes time to adjust the level of humidity to the target humidity H0. However, the humidity can be adjusted silently.

If the humidity inside the cell 2 is lower than the target humidity due to excessive dehumidification (NO in step S34), humidification may be performed in the case of the humidity controller 6 having a humidifying function. However, in the case of a humidity controller having no humidifying function, if the opening direction of the valve 5b is controlled such that the air supply and exhaust opening 3b communicates with the external air, the water vapor in the external air gradually enters the cell 2 and, thus, the humidity in the cell 2 increases. The measurement of the humidity H is repeated until the expression H−H0>−ε is satisfied, and the humidity control process ends.

Referring back to FIG. 3, the description of the training process is continued.

The control unit 10 acquires, as a third response value, the response value of the gas sensor at the end of the humidity control process (step S13).

The control unit 10 controls the opening direction of the valve 5a so as to connect the air supply and exhaust opening 3a to the gas inlet 7 and controls the opening direction of the valve 5b so as to cause the air supply and exhaust opening 3b to communicate with the external air. The control unit 10 introduces the artificial exhaled air into the cell 2 through the gas inlet 7 and discharges the artificial exhaled air to the outside through the air supply and exhaust opening 3b and the valve 5b. As a result, the artificial exhaled air is introduced into the cell 2 at a predetermined flow rate for a predetermined period of time (step S14).

The control unit 10 lets the gas in the cell 2 sit for a certain period of time after the introduction of the artificial exhaled air and acquires, as a fourth response value, the maximum one of the response values with respect to each of the gas sensors during the period of time from the introduction of the artificial exhaled air to the end of the artificial exhaled being left sitting (step S15).

The control unit 10 sets the third response value and the fourth response value obtained in this manner as the base value and the peak value, respectively, and sets the difference between the base value and the peak value (for example, the delta or the ratio of the peak value to the base value) as an effective response value of the gas sensor. In this manner, if drift of the characteristics of a gas sensor element itself and/or drift of an analog circuit that converts the response value of the gas sensor (for example, the element resistance value of a semiconductor gas sensor) into a voltage occurs, the drift can be cancelled as much as possible.

The control unit 10 obtains the base values and the peak values for all the artificial exhaled airs, obtains the effective response values of the gas sensor and obtains the correspondence information indicating the relationship between the gas concentration and the effective response value of the gas sensor.

Thereafter, the control unit 10 records the correspondence information in the data recording unit 30 (step S17). The correspondence information may be, for example, mathematical expressions or numerical tables representing the inverse functions $f_1^{-1}$, $f_2^{-1}$, and $f_3^{-1}$ described in FIG. 14. Alternatively, the correspondence information may be configuration information of the neural network that executes the inverse functions $f_1^{-1}$, $f_2^{-1}$, and $f_3^{-1}$. Furthermore, the base values, the peak values, and the effective response values of the response values of the gas sensor may be recorded in the data recording unit 30.

The effect of controlling the humidity in the cell 2 to a constant target humidity before the third response value is acquired in step S12 is described below.

Figure 7:
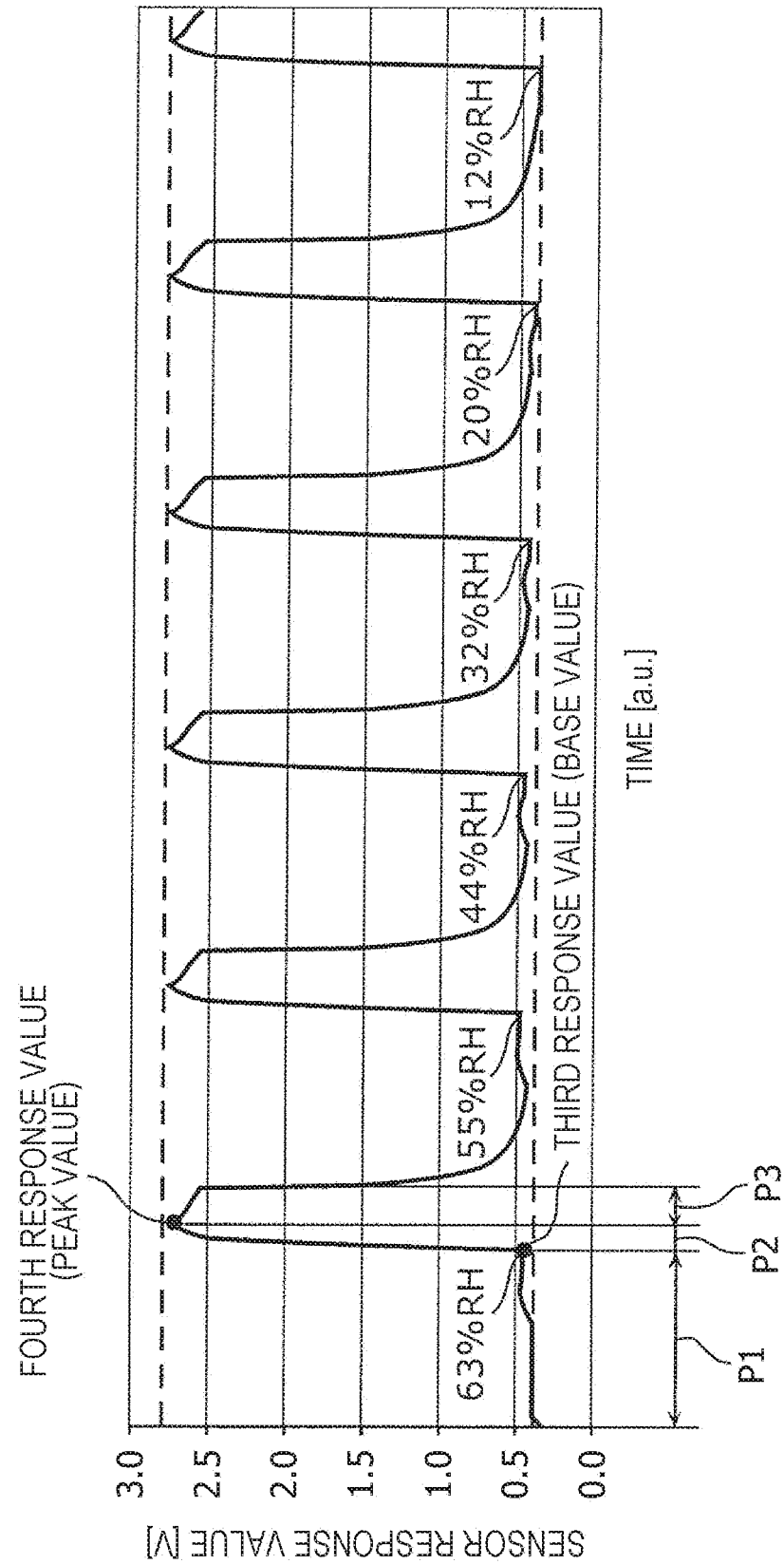
FIG. 7 is a graph illustrating an example of response values of a gas sensor for the artificial exhaled air.

FIG. 7 is a graph illustrating an example of the response value of the gas sensor for the artificial exhaled air. In FIG. 7, the ordinate represents the gas sensor output voltage of the semiconductor gas sensor (the hydrogen sensor SB-19 available from NISSHA FIS, Inc.) for the artificial exhaled air, and the abscissa represents the time.

FIG. 7 illustrates the result of the gas sensor output voltage obtained when the following process is performed six times: ventilation with the external air and humidity control by dehumidification are performed in the cell 2 (a period P1), the artificial exhaled air is introduced at a constant flow rate for a certain period of time (a period P2), and the gas is left sitting in the cell 2 for a certain period of time (a period P3). The artificial exhaled air is air which is a mixture of 1.0 ppm of acetone, 1.2 ppm of ethanol, 24.8 ppm of hydrogen, 6.2 ppm of carbon monoxide, and 25.4% of carbon dioxide. In addition, the air has a relative humidity of about 70%.

Through all the iterations of the process, the target humidity in the humidity control is intentionally decreased from 63% RH to 12% RH. This range of humidity includes the annual range of seasonal variations of the humidity in Japan. That is, the values in the result illustrated in FIG. 7 correspond to the response values of the gas sensor observed without performing humidity control throughout the year.

As can be clearly seen from FIG. 7, the base value of the response voltage of the gas sensor varies in accordance with the level of humidity. That is, the gas sensor has humidity dependence. For this reason, if the difference between the base value and the peak value obtained without performing humidity control is used as the effective value of the response value of the gas sensor, the effective value of the response value also has humidity dependence. Such humidity dependence is reduced by controlling the humidity inside the cell 2 to a certain humidity before acquiring the base value of the response value of the gas sensor.

For example, if the target humidity in humidity control is set to 10% RH, the environmental humidity exceeds this value throughout the year, so that the humidity inside the cell 2 can be controlled to 10% RH only by performing dehumidification. To reduce the period of time required for humidity control, the target humidity may be set to 20% RH. If the humidity controller 6 having a humidifying function is used, the humidity value may be controlled so as to increase by humidification. However, the humidifying function is not always necessary. By removing the humidifying function, a complicated configuration of the apparatus can be avoided.

Still alternatively, the humidity controller 6 itself may be removed, and air having a humidity preset to a constant value or an inert gas, such as nitrogen gas, may be introduced by using a gas cylinder or a spray can. However, assuming that the equipment is widely used in households and is carried outside the home, it is difficult to always have a gas cylinders and spray can on hand. Therefore, employing a method for acquiring dry air with a humidity controller having only a dehumidifying function is more practical.

The inventor has also verified that humidity control performed on the exhaled air itself is not needed to obtain the peak value in measuring the exhaled air.

Figure 8:
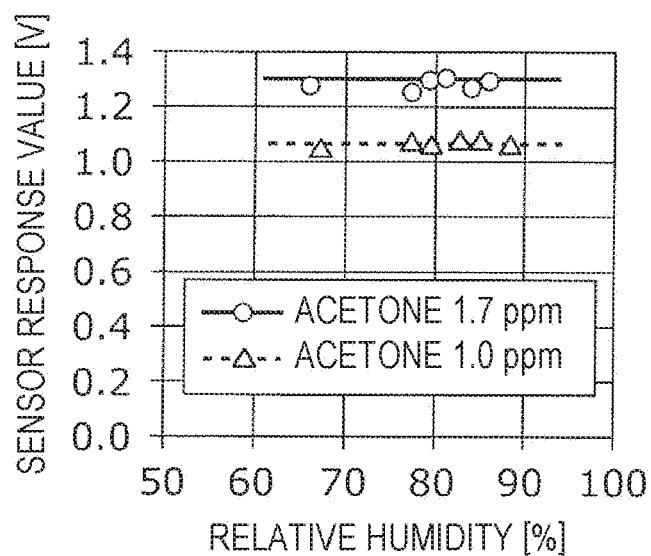
FIG. 8 is a graph illustrating an example of response values of the gas sensor for the artificial exhaled air.

FIG. 8 illustrates the relationship between the response value of a gas sensor that mainly detects acetone to a mixed gas containing acetone and water vapor and the relative humidity. As can be seen from FIG. 8, in the high humidity region having a relative humidity of 80% or higher which is considered as the exhaled air, the response of the gas sensor is constant, and the difference between 1.0 ppm and 1.7 ppm of acetone can be discerned.

In other words, in a high humidity region, such as exhaled air, the humidity dependence of the response value of the gas sensor to acetone is small, so that the humidity dependence of the peak value of the obtained response value is small even if the humidity of the exhaled air itself is not controlled. Such characteristics are also found in gas sensors that mainly detect a gas other than acetone.

Therefore, by controlling the humidity in the cell when acquiring the base value, not the peak value, of the response value of the gas sensor, a great effect can be obtained. That is, the humidity dependence of the gas sensor can be effectively reduced by acquiring the base value while the humidity is controlled to be constant.

The effect of introducing the artificial exhaled air into the cell 2 at a predetermined flow rate for a predetermined of time in step S14 is described below.

Figure 9:
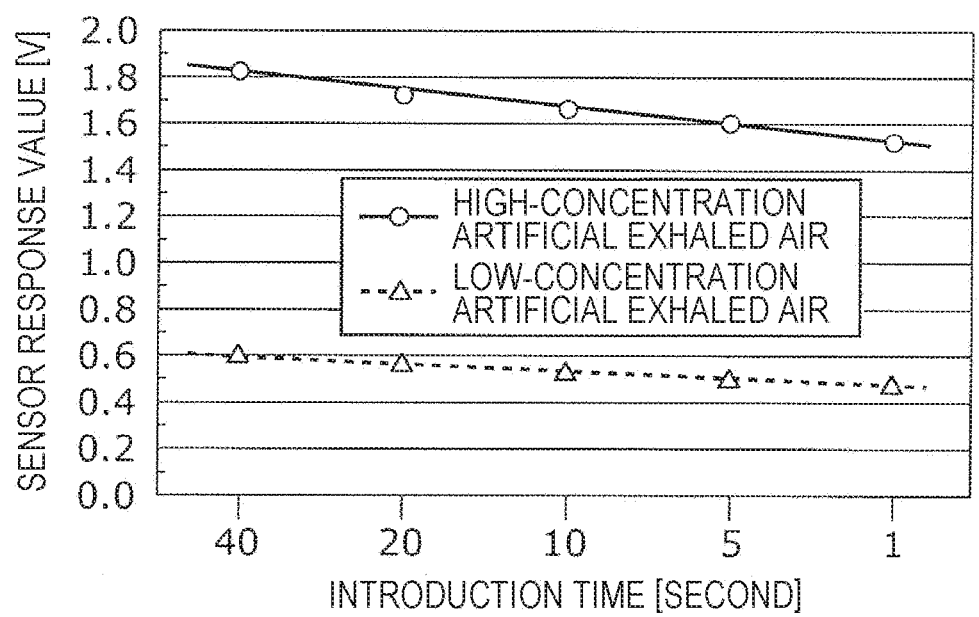
FIG. 9 is a graph illustrating an example of response values of the gas sensor for the introduction time of the artificial exhaled air.

FIG. 9 is a graph illustrating an example of the response value of the gas sensor versus the introduction time of the artificial exhaled air. In FIG. 9, the ordinate represents the effective response value (the difference between the base value and the peak value) of the gas sensor, and the abscissa represents the introduction time of the artificial exhaled air. FIG. 9 illustrates the effective response values obtained when two types of artificial exhaled airs (high-concentration artificial exhaled air and low-concentration artificial exhaled air) having different concentrations of a constituent gas are introduced at a flow rate of 2.3 L/min for 40 seconds, 20 seconds, 10 seconds, 5 seconds, and 1 second.

As can be seen from FIG. 9, the response value of the gas sensor varies in accordance with the blowing time for any one of the artificial exhaled airs having different constituent gas concentrations. The total amount of gas introduced is the product of the flow rate and the introduction time. Consequently, by normalizing both the gas flow rate and the gas introduction time, effective correspondence information can be obtained in step S17.

As described above, in the training process S10, the response value of the gas sensor having a humidity dependence reduced by controlling the humidity in the cell is obtained, and the correspondence information between the gas concentration and the effective response value of the gas sensor is obtained. In addition, the response value of the gas sensor has a dependence on the gas introduction flow rate and the gas introduction time.

The actual measurement process S20 is described below in the light of the dependence of the gas sensor on the humidity and the dependence on the gas introduction flow rate and introduction time.

Inmost of the actual measurement process S20, the artificial exhaled air in the training process S10 is replaced with an actual exhaled air to be measured. Note that the artificial exhaled air to be measured is an example of a first gas.

Referring back to FIG. 3, in step S21, the control unit 10 drives the pump 4 and controls the opening direction of the valve 5a so that the pump 4 can suck the gas in cell 2. In addition, the control unit 10 controls the opening direction of the valve 5b so that the external air can be drawn into the cell 2 without passing through the humidity controller 6. In this manner, the inside of the cell 2 is ventilated with the external air, so that the constituent gases of the exhaled air and water vapor remaining in the cell are discharged.

Subsequently, the control unit 10 controls the opening direction of the valve 5b so that the external air can be drawn into the cell 2 via the humidity controller 6. As a result, the constituent gases of the exhaled air remaining in the cell 2 are further discharged to facilitate dehumidification. Note that the external air drawn into the cell 2 after being humidified or dehumidified by the humidity controller 6 is an example of a second gas.

In step S21, the humidity in the cell 2 is controlled so as to be the same as the target humidity set in the humidity control performed in step S12 of the training process S10. In this way, the measurement accuracy can be improved. At this time, the target humidity may be a relative humidity or an absolute humidity. In addition, the target humidity may be a humidity within a predetermined range. As in the training process S10, the procedure illustrated in FIG. 5 is applied to the humidity control. If the humidity inside of the cell 2 reaches the target humidity range, the control unit 10 ends the humidity control and notifies the user that the humidity reaches the target humidity range via the display unit 20 serving as a humidity display unit.

Figure 10:
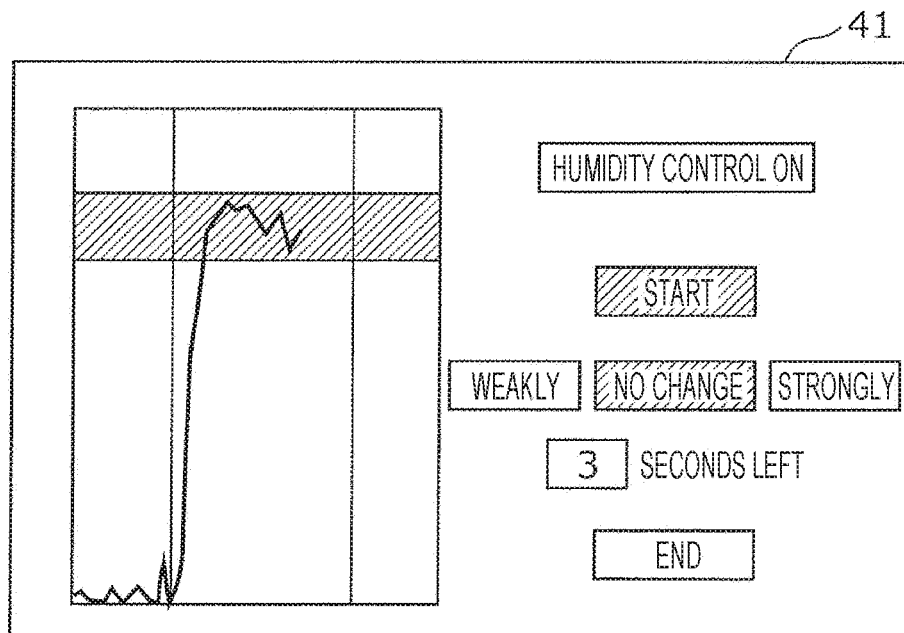
FIG. 10 is a diagram illustrating an example of an operation guide screen according to the first embodiment.

FIG. 10 is a diagram illustrating an example of an operation guide screen displayed on the display unit 20. In the operation guide screen illustrated in FIG. 10, the "humidity control on" icon is displayed with high brightness while the humidity is being controlled.

Like the third response value in the training process S10, the control unit 10 acquires, as a first response value, the response value of the gas sensor when the humidity control ends (step S22). After the first response value is acquired, the "humidity control on" icon is displayed with low brightness, and the "start" icon is displayed with high brightness in the operation guide screen of the display unit 20 (step S23). As a result, the user recognizes that they can now blow exhaled air into the apparatus.

In step S24, the control unit 10 controls the opening direction of the valve 5a so that the air supply and exhaust opening 3a is connected to the gas inlet 7. The control unit 10 controls the opening direction of the valve 5b so that the air supply and exhaust opening 3b communicates with the external air. The user blows exhaled air into the cell 2 through the gas inlet 7, and the gas blown into the cell 2 is discharged to the outside through the air supply and exhaust opening 3b and the valve 5b.

When, as illustrated in FIG. 10, the user starts blowing exhaled air, the value output from the flow rate detector 1e disposed in the cell 2 is presented in the operation guide screen of the display unit 20 in the form of a graph in real time. For example, in the operation guide screen, a flow rate range of ±10% of the introduction flow rate in step S14 of the training process S10 is indicated with hatching, and the user is guided so that the flow rate of the exhaled air is within the range indicated with hatching. For example, icons, such as "weakly", "no change", and "strongly", may be arranged on the right side of the screen, and one of the icons may be displayed with high brightness in accordance with an increase/decrease in the flow rate of exhaled air.

The user can control the blowing flow rate in accordance with the presented guide and blow the exhaled air at a constant flow rate. The control unit 10 detects the rise of the value output from the flow rate detector 1e caused by the blowing of exhaled air, measures the elapsed time from the detection point in time. When a period of time equal to the introduction time in step S14 elapses, the control unit 10 performs control so that the exhaled air blown into the cell 2 is blocked by the valve 5a (step S25).

In this way, the blowing flow rate and the blowing time of the exhaled air in step S24 are controlled so as to be the same as the introduction flow rate and the introduction time, respectively, obtained when the artificial exhaled air is introduced in step S14 of the training process S10. As a result, the dependence of the response value of the gas sensor on the gas introduction flow rate and the gas introduction time can be reduced.

After the introduction of the exhaled air ends, the control unit 10 lets the gas in the cell 2 sit for a certain period of time and, thereafter, acquires, as a second response value, the maximum one of the response values with respect to each of the gas sensors obtained during the period of time from the start of blowing of the exhaled air to the end of the exhaled air being left sitting (step S26).

The control unit 10 regards the first response value and the second response value obtained in this manner as the base value and the peak value, respectively, and sets the difference between the base value and the peak value (the delta or the ratio of the peak value to the base value) as an effective response value of the gas sensor.

The control unit 10 calculates the concentration of a constituent gas contained in the exhaled air by using the effective response value of the gas sensor and the correspondence information stored in the data recording unit 30 (step S27). The calculated concentration is presented to the user via a measurement result screen displayed on the display unit 20 (step S28).

Figure 11:
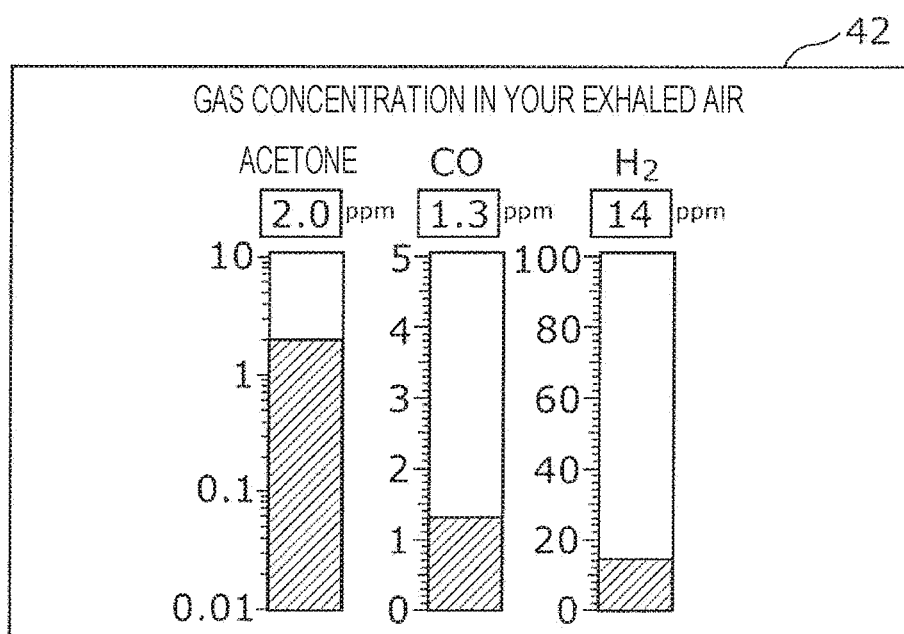
FIG. 11 is a diagram illustrating an example of a measurement result screen according to the first embodiment.

FIG. 11 is a diagram illustrating an example of the measurement result screen displayed on the display unit 20. More specifically, in the result illustrated in FIG. 11, the gas sensor 1a serves as an acetone sensor (SB-AQ8 available from NISSHA FIS, Inc.), the gas sensor 1b serves as a hydrogen sensor (SB-19 available from NISSHA FIS, Inc.), and the gas sensor 1c serves as a carbon monoxide sensor (TGS5042 available from FIGARO Engineering Inc.). The results obtained after the concentrations of the three types of constituent gases are measured by using the three gas sensors are illustrated in FIG. 11.

As described above, in the actual measurement process S20, the response value of the gas sensor having a reduced humidity dependence is obtained by controlling the humidity in the cell. Thus, the gas concentration can be obtained with high accuracy by using the effective response value of the gas sensor and the correspondence information. In addition, the dependence of the response value of the gas sensor on the introduction flow rate and the introduction time of the gas can be reduced by setting the blowing flow rate and the blowing time of the exhaled air of the user to be the same as the introduction flow rate and the introduction time of the artificial exhaled air in the training process S10 as much as possible.

The effect of controlling the humidity in step S21 of the actual measurement process S20 is described below with reference to comparison of three effective response values of the gas sensor, first one of which is obtained when humidity control is not performed, second one of which is obtained by performing when only ventilation is performed, and third one of which is obtained when humidity control through dehumidification is performed.

Figure 12A:
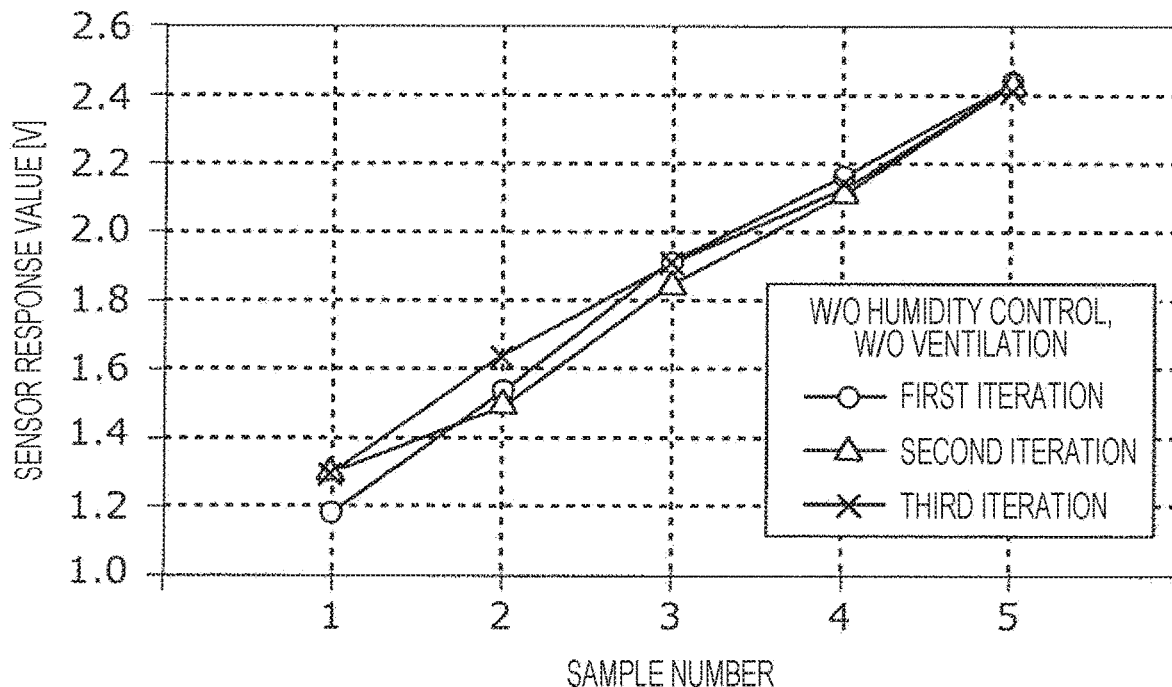
FIG. 12A is a graph illustrating an example of the repetitive reproducibility of a response value output from a gas sensor in accordance with the presence/absence of humidity control.
Figure 12B:
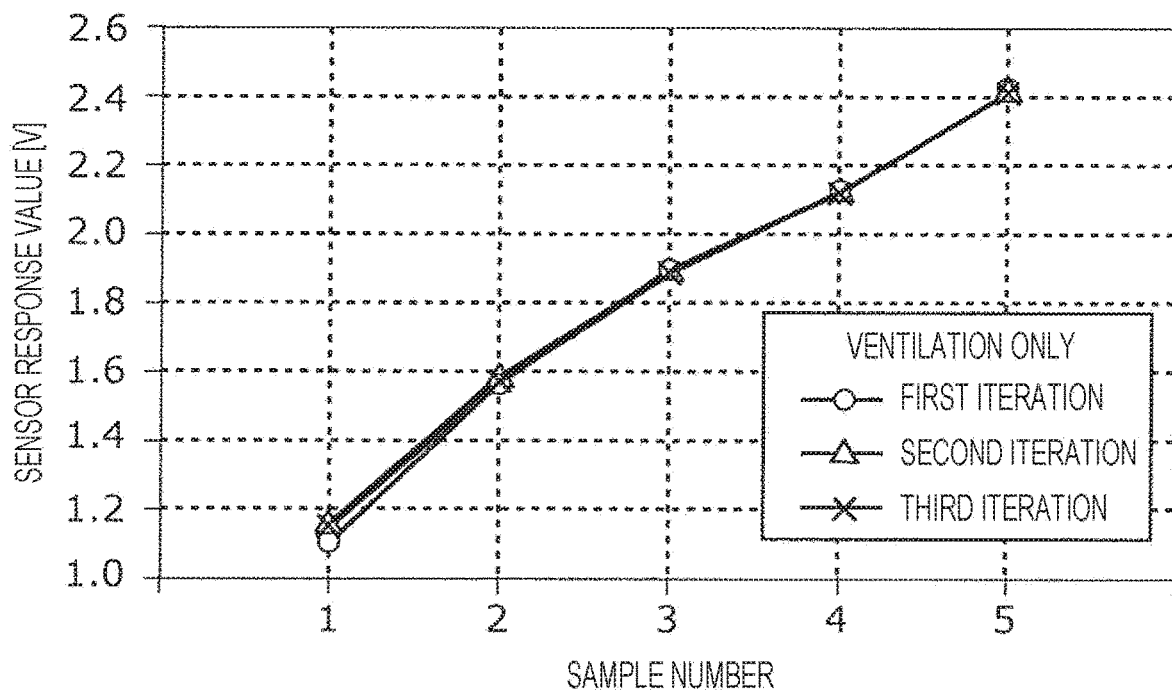
FIG. 12B is a graph illustrating an example of the repetitive reproducibility of a response value output from a gas sensor in accordance with the presence/absence of humidity control.
Figure 12C:
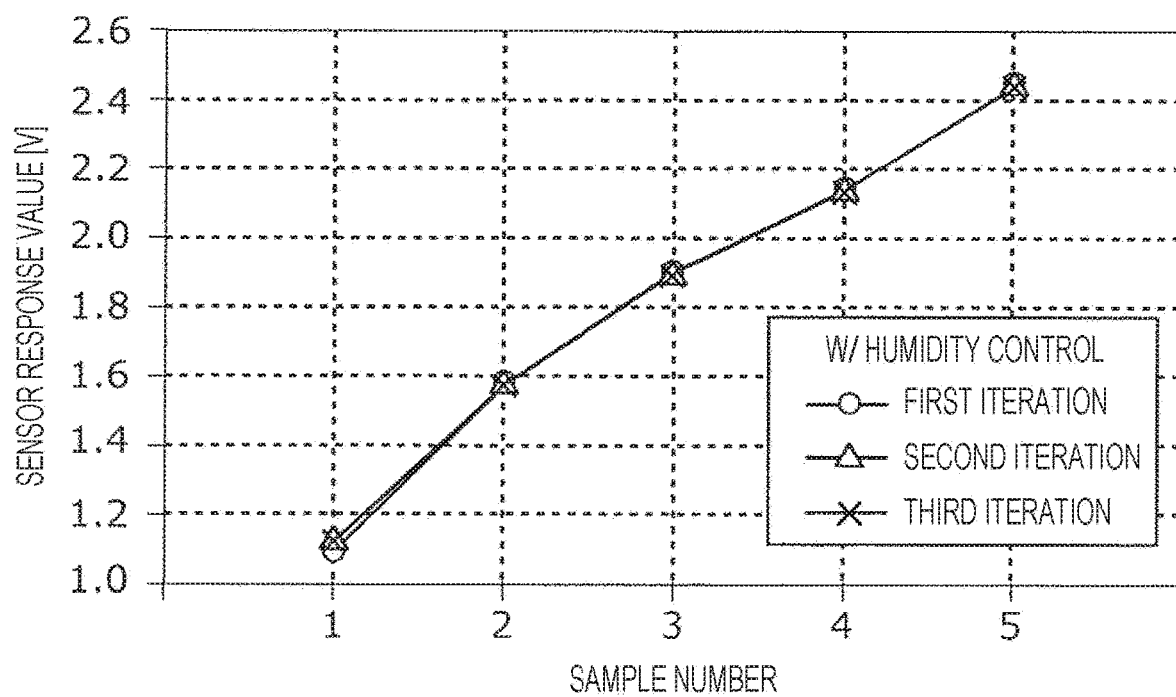
FIG. 12C is a graph illustrating an example of the repetitive reproducibility of a response value output from a gas sensor in accordance with the presence/absence of humidity control.

FIGS. 12A, 12B, and 12C are graphs illustrating an example of repetitive reproducibility of the response value of the gas sensor in accordance with the presence or absence of humidity control. In FIGS. 12A, 12B, and 12C, the ordinate represents the response value (the peak value) of the gas sensor, and the abscissa represents the sample number of artificial exhaled air. The sample of artificial exhaled air contains a constituent gas of a higher concentration with increasing sample number.

FIGS. 12A, 12B, and 12C illustrate the response value (the peak value) of the gas sensor when the process of introducing the samples of artificial exhaled air into the cell 2 in the order of sample number 1, 2, 3, 4, 5, 4, 3, 2, and 1 (that is, in the order in which the sample number increases and, thereafter, decreases) is repeated three times. For comparison, FIG. 12A illustrates the result in the case where the humidity control in step S21 is eliminated. FIG. 12B illustrates the result in the case where only ventilation with external air is performed instead of performing the humidity control in step S21. FIG. 12C illustrates the result in the case where humidity control through dehumidification is performed in step S21.

In FIG. 12A, the response values are significantly different between when the concentration is increased and when the concentration is decreased in different iterations or even the same iteration. That is, the repetitive reproducibility of the response values cannot be obtained. In FIG. 12B, the repetitive reproducibility of the response value is improved as compared with in FIG. 12A, but it is not sufficient. In FIG. 12C, almost the same response value is reproduced when the concentration is increased and when the concentration is decreased in different iterations or the same iteration. That is, practical repetitive reproducibility is obtained.

Figure 12D:
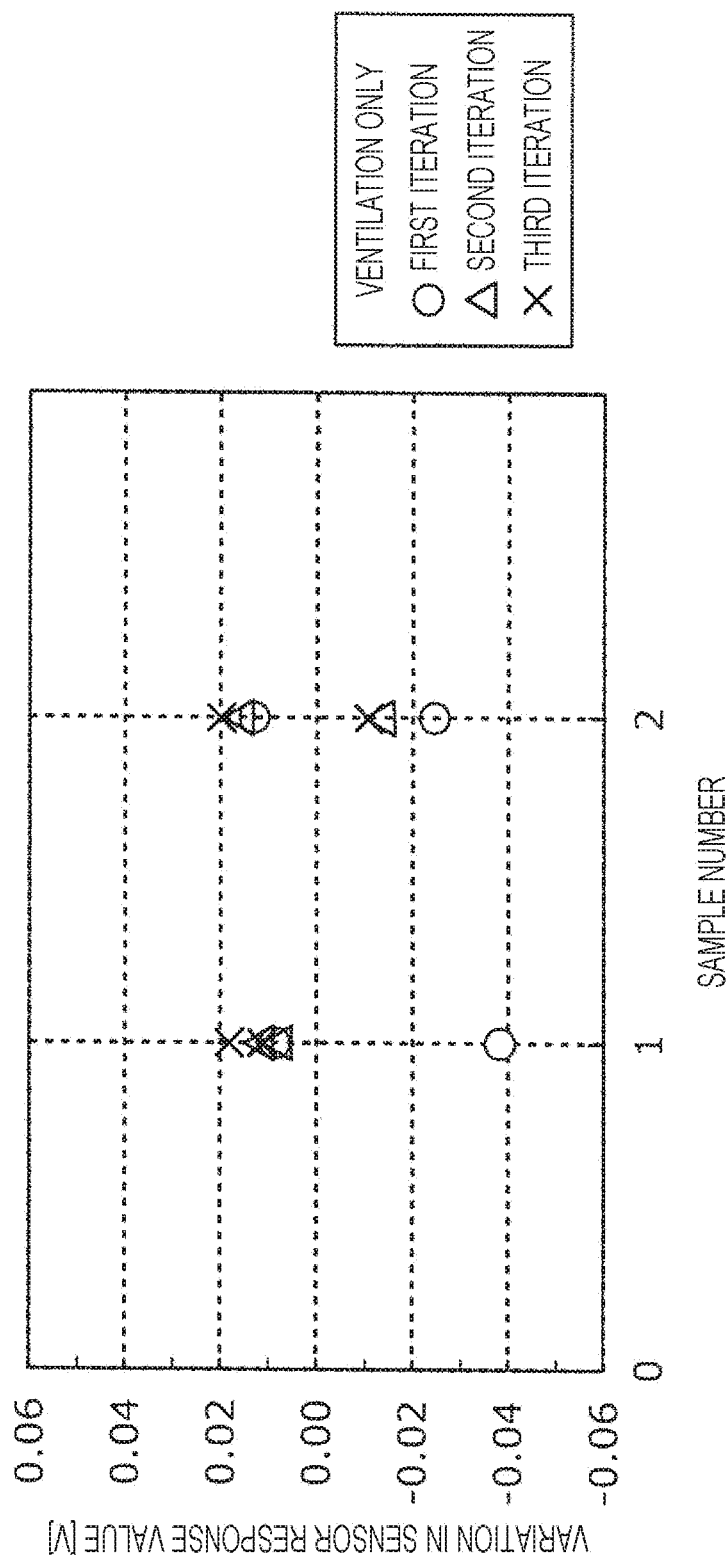
FIG. 12D is a graph illustrating an example of the repetitive reproducibility of a response value output from a gas sensor in accordance with the presence/absence of humidity control (a graph in which the variation in repetitive reproducibility in FIG. 12B is enlarged for sample numbers 1 and 2 at low concentration condition)

More specifically, FIG. 12D illustrates the variation in the sensor response values (that is, the difference from the average) in the low concentration region (that is, the region corresponding to sample numbers 1 and 2) in FIG. 12B. FIG. 12E illustrates the variation in the sensor response values in the low concentration region in FIG. 12C. The variation in FIG. 12E in which humidity control is performed is lower than that in FIG. 12D in which only ventilation is performed. That is, higher repetitive reproducibility is obtained by controlling the humidity.

From the above-described results, by controlling the humidity in the cell 2 to a constant value in step S21, practical repetitive reproducibility can be obtained in the actual measurement process S20.

Note that while the above example has been described with reference to exhaled gas as the gas to be measured, the gas constituent measuring apparatus according to the present embodiment is also applicable to skin gas. Even in this case, the gas constituent measuring apparatus has a configuration the same as that of the above-described exhaled air constituent measuring apparatus and operates in the same manner, except for the points described below. That is, unlike exhaled gas, skin gas does not have a pressure source like the lungs. For this reason, the gas constituent measuring apparatus is configured to receive, for example, a minute amount of gas diffusing from the skin surface by using a micro-capacity cell over time. The skin gas is diffused at a flow rate below the detection lower limit of the flow rate sensor that constitutes the flow rate detector 1e illustrated in FIG. 1. In this case, to make the flow rate of the gas flowing into the cell constant, the skin is exposed to the gas inlet 7, for example. The valve 5a is driven so that the gas inlet 7 communicates with the air supply and exhaust opening 3a and, thereafter, measurement is carried out for a predetermined period of time. Subsequently, communication is blocked. That is, in this case, the flow rate detector 1e may have only the function of measuring predetermined period of time.

Therefore, the process in step S14 of the training process S10 illustrated in FIG. 3 may be started and ended only by time management without using the flow rate management. Similarly, in step S23 of the actual measurement process S20, instead of presenting the blowing flow rate to the user, the elapsed time may be presented to the user until the predetermined period of time, which is the same as in the training process, elapses after the skin is exposed to the gas inlet 7 and, thereafter, the valve 5a is driven so that the gas inlet 7 communicates with the air supply and exhaust opening 3a. In addition, in step S11 of the training process S10 in which artificial skin gas is generated, instead of directly leading, to the gas inlet 7, the pressure of the mixed gas generated by the artificial exhaled air generating apparatus illustrated in FIG. 4, the artificial skin gas may be temporarily collected in a gas bag or the like. Subsequently, the artificial skin gas in a gas bag having a pressure the same as the atmospheric pressure may be connected to the gas inlet 7.

Second Embodiment

A gas constituent measuring apparatus according to the second embodiment is described below with reference to an example of an exhaled air constituent measuring apparatus formed on a toothbrush and a cradle of the toothbrush.

The exhaled air constituent measuring apparatus according to the second embodiment is an application example in which the exhaled air constituent measuring apparatus described in the first embodiment is formed on a toothbrush and a cradle of the toothbrush. The reason why the exhaled air constituent measuring apparatus is formed on a toothbrush is that the toothbrush is a household item that can be held in the mouth and, thus, has a high affinity for the action of blowing the exhaled air thereinto.

Figure 13:
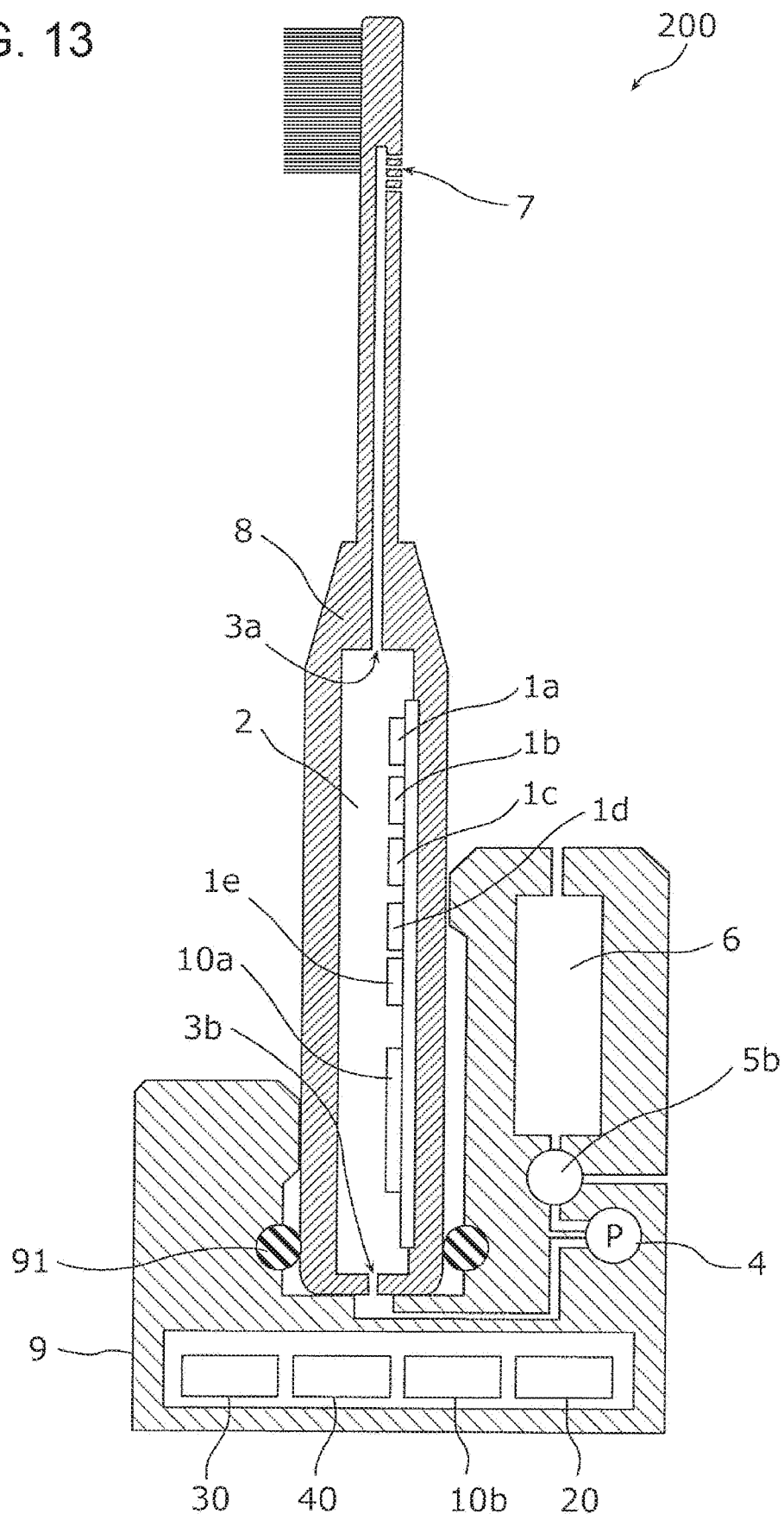
FIG. 13 is a schematic illustration of an example of the functional configuration of an exhaled air constituent measuring apparatus according to a second embodiment.

FIG. 13 is a schematic illustration of an example of the functional configuration of the exhaled air constituent measuring apparatus according to the second embodiment. As illustrated in FIG. 13, an exhaled air constituent measuring apparatus 200 is formed on a toothbrush 8 and a cradle 9 that holds the toothbrush 8. In the following description, the constituent elements of the exhaled air constituent measuring apparatus 200 are designated by the same reference numerals as the functionally corresponding constituent elements of the exhaled air constituent measuring apparatus 100. Furthermore, the description of the items common to the items described for the exhaled air constituent measuring apparatus 100 is not repeated as needed.

The toothbrush 8 is provided with gas sensors 1a, 1b, 1c, a humidity sensor 1d, a flow rate detector 1e, a cell 2, air supply and exhaust openings 3a and 3b, a gas inlet 7, and a control unit 10a.

The cell 2 is configured by the internal space of a grip portion of the toothbrush 8. The gas sensors 1a, 1b, and 1c, the humidity sensor 1d, the flow rate detector 1e, and the control unit 10a are disposed in the internal space.

The flow rate detector 1e is configured by a pressure sensor that detects the pressure inside the cell 2. From the detected pressure and the design value of the flow path resistance against the exhaled air in the toothbrush 8, the blowing flow rate of the exhaled air is calculated. In general, a diaphragm-based pressure sensor is more inexpensive and has a simpler configuration than a hot wire gas flow rate detector and an ultrasonic gas flow rate detector. In addition, a diaphragm-based pressure sensor is easily accommodated in a small volume, such as the volume of a toothbrush.

The gas inlet 7 is provided in the vicinity of the brush of the toothbrush 8 and is formed of a set of water-repellent fine holes so that water does not enter the inside of the toothbrush during brushing. The exhaled air blown through the gas inlet 7 is introduced into the cell 2 and is discharged from the air supply and exhaust opening 3b.

The control unit 10a is configured by, for example, a one-chip microcomputer. The control unit 10a controls driving of a variety of sensors and acquisition of measurement values with the toothbrush 8 being removed from the cradle 9.

The cradle 9 is provided with a pump 4, a valve 5b, a humidity controller 6, a control unit 10b, a display unit 20, a data recording unit 30, a data analysis unit 40, and an O-ring 91.

The humidity controller 6 is a cylinder containing a desiccant, such as silica gel or molecular sieve. The humidity controller 6 has only a dehumidifying function.

The O-ring 91 maintains airtightness between the toothbrush 8 and the cradle 9.

The control unit 10b, the data recording unit 30, and the data analysis unit 40 are configured by, for example, a one-chip microcomputer. The display unit 20 is composed of, for example, a sounding element, such as a piezoelectric buzzer, and a light emitting element, such as a light emitting diode.

The control unit 10a provided in the toothbrush 8 and the control unit 10b provided in the cradle 9 operate simultaneously via, for example, wireless communication. In the exhaled air constituent measuring apparatus 200, the control unit 10a and the control unit 10b operate simultaneously so as to function as the control unit 10 in the exhaled air constituent measuring apparatus 100.

An example of the operation performed by the exhaled air constituent measuring apparatus 200 is described below.

Instead of controlling the humidity before measuring artificial exhaled air and measuring the exhaled air of the user, the humidity may be controlled after measuring the artificial exhaled air and after measuring the exhaled air of the user. That is, in acquiring the response value of the gas sensor, the peak value is acquired first and, thereafter, the base value is acquired in each of the training process and the actual measurement process so that the humidity control is performed after measuring the artificial exhaled air and the exhaled air of the user. As a result, in the case where an exhaled air constituent is detected while the user is brushing the teeth, the user need not wait and, thus, the convenience of the user can be improved.

The training process performed by the exhaled air constituent measuring apparatus 200 is described first.

In the training process performed by the exhaled air constituent measuring apparatus 200, steps S14 and S15 of the training process S10 illustrated in FIG. 3 are performed before steps S12 and S13 are performed. As a result, the peak value of the response value of the gas sensor to the artificial exhaled air is acquired first and, thereafter, humidity control is performed. Subsequently, the base value is acquired. In step S17, the difference between the acquired base value and the peak value is defined as the effective response value of the gas sensor, and correspondence information indicating the relationship between the gas concentration and the effective response value of the gas sensor is recorded in the data recording unit 30.

By performing steps S14 and S15 before steps S12 and S13 are performed, the user can measure the artificial exhaled air without waiting for humidity control.

Subsequently, the actual measurement process performed by the exhaled air constituent measuring apparatus 200 is described.

In the actual measurement process performed by the exhaled air constituent measuring apparatus 200, steps S23 to S26 of the actual measurement process S20 illustrated in FIG. 3 are performed before steps S21 and S22 are performed.

In the actual measurement process performed by the exhaled air constituent measuring apparatus 200, after finishing brushing the teeth, the user holds the gas inlet 7 in their mouth first. Thereafter, the user blows the exhaled air into the gas inlet 7. The constituent gas of the exhaled gas introduced from the gas inlet 7 is detected by the gas sensors 1a, 1b, and 1c disposed in the cell 2. The start of blowing the exhaled air into the gas inlet 7 is detected by the response of the pressure sensor serving as the flow rate detector 1e.

A microprocessor, which is the control unit 10a, detects the start of blowing the exhaled air by the flow rate detector 1e and informs, via the display unit 20, the user of whether the pressure value is within a predetermined range during blowing and whether blowing continues for a predetermined period of time.

After completion of blowing, the exhaled air is left sitting in the cell 2 for a certain period of time. The maximum one of the response values with respect to each of the gas sensors 1a, 1b, and 1c acquired during the period of time from the start of blowing to the end of the exhaled air being left sitting is defined as a second response value.

In the exhaled air constituent measuring apparatus 200, the valve 5a or a shutter is not provided at the air supply and exhaust opening 3a so that the cell 2 is not blocked from the outside after blowing. Instead, the diameter of the air supply and exhaust opening 3a is made sufficiently small and, thus, the exhaled air constituent measuring apparatus 200 acquires the response values of the gas sensors 1a, 1b, and 1c without being influenced by the external air.

The above-described processing corresponds to steps S23 to S26 in FIG. 3. By performing steps S23 to S26 before steps S21 and S22 are performed, the user can measure their exhaled air without waiting for the humidity control.

Subsequently, the user returns the toothbrush 8 to the cradle 9 and enables the air supply and exhaust opening 3b located at the base of the toothbrush 8 to communicate with the inside of the cradle 9. Subsequently, the user starts the pump 4 to draw external air into the cradle through the air supply and exhaust opening of the cradle 9 and send the external air to the toothbrush 8 to ventilate the inside of the cell 2 for a certain period of time.

At this time, the humidity in the cell 2 is monitored by a humidity sensor 4d. If the humidity does not reach the prescribed humidity by ventilation only, the direction of the valve 5b is switched to draw external air into the cradle 9 through the humidity controller 6 and send the external air to the toothbrush 8. Thus, the humidity inside the cell 2 is controlled to the predetermined level.

To control the humidity, the procedure illustrated in FIG. 5 is used. If the humidity inside of the cell 2 reaches the target humidity range, the humidity control ends, and the base value of the response value of the gas sensor is obtained as the first response value. By obtaining the first response value, the effective response value of the gas sensor is obtained by calculating the difference between the first response value and the second response value.

The above-described processing corresponds to steps S21 and S22 illustrated in FIG. 3.

Finally, the concentration of the constituent gas of the exhaled air is determined. This processing corresponds to steps S27 and S28 illustrated in FIG. 3. In the exhaled air constituent measuring apparatus 200, the first response value, which is the base value, and the second response value, which is the peak value, are sent to the data analysis unit 40 by, for example, wireless communication between the toothbrush 8 and the cradle 9. The data analysis unit 40 determines the concentration of the constituent gas of the exhaled air on the basis of the correspondence information recorded in the data recording unit 30.

As a modification of the second embodiment, the data recording unit 30, the data analysis unit 40, the control unit 10b, the pump 4, the valve 5b, and the humidity controller 6 provided in the cradle 9 in FIG. 13 may be all miniaturized so as to be stored in the toothbrush 8.

In the present disclosure, all or some of the units or all or some of the functional blocks in the block diagrams illustrated in FIGS. 1 and 13 may be executed by a single or a plurality of electronic circuits including a semiconductor device, a semiconductor integrated circuit (IC), or an LSI (large scale integration). The LSIs or ICs may be integrated into one chip or may be configured by combining a plurality of chips. The terms "LSI" and "IC" are used herein, the terms may change in accordance with the level of integration, and the terms "system LSI", "VLSI (very large scale integration)", and "ULSI (ultra large scale integration)" may be used. A Field Programmable Gate Array (FPGA), which is programmed after the manufacture of the LSI, or a reconfigurable logic device capable of reconfiguring the bonding relation inside the LSI or setting up the circuit partitions inside an LSI can be used for the same purpose.

Furthermore, the functions or operations of all or some of the units can be executed by software processing. In this case, the software is recorded on one or more non-transitory recording media, such as a semiconductor memory, an optical disk, and a hard disk drive. If the software is executed by a processing apparatus (a processor), the function identified by the software is performed by the processing apparatus (the processor) and peripheral devices. The apparatus according to the present disclosure may include one or more non-transitory recording media on which the software is recorded, processors, and required hardware devices, such as interfaces.

The gas constituent measuring apparatus according to the present disclosure can be widely used in, for example, the field of healthcare as an inexpensive exhaled air constituent measuring apparatus that is simple in configuration and control.

What is claimed is:

1. A gas constituent measuring apparatus comprising:
a cell that draws in a first gas to be measured;
a gas sensor that responds to one or more types of constituent gases present in the cell;
a regulator that controls humidity in the cell;
a humidity sensor that detects the humidity in the cell; and
an integrated circuit,
wherein the integrated circuit is configured to:
control the regulator on the basis of a result of detection of the humidity sensor so that the humidity in the cell is within a predetermined range before the first gas is drawn into the cell or after the first gas is discharged from the cell,
acquire a first response value output from the gas sensor for the inside of the cell having a humidity controlled through the control performed on the regulator,
acquire a second response value output from the gas sensor for the first gas drawn into the cell after the first gas is drawn into the cell without controlling to maintain the humidity of the inside of the cell, and
determine wherein the integrated circuit determines concentrations of each of the one or more types of constituent gases on the basis of the first response value and the second response value.

2. The gas constituent measuring apparatus according to claim 1, wherein:
the regulator includes
at least one of a humidifier and a dehumidifier, and
a pump that introduces, into the cell, a second gas humidified by the humidifier or dehumidified by the dehumidifier, and
the integrated circuit is configured to control the introduction of the second gas into the cell so that the humidity in the cell is within the predetermined range.

3. The gas constituent measuring apparatus according to claim 2, wherein the humidifier or the dehumidifier draws in air outside the gas constituent measuring apparatus and humidifies or dehumidifies the drawn air as the second gas.

4. The gas constituent measuring apparatus according to claim 2, wherein the regulator includes a valve that opens or closes a flow of the second gas introduced into the cell.

5. The gas constituent measuring apparatus according to claim 2,
wherein the cell has a plurality of openings including a first opening and a second opening that differs from the first opening,
wherein the first gas is drawn into the cell through the first opening, and
wherein the second gas is introduced into the cell through the second opening.

6. The gas constituent measuring apparatus according to claim 2,
wherein the cell includes a first gas inlet for drawing the first gas and a second gas inlet for drawing the second gas located at a position on the cell different from the first inlet.

7. The gas constituent measuring apparatus according to claim 6, wherein:
the cell has a cylinder shape, and the first gas inlet and the gas second inlet are disposed at both ends of the cell, respectively.

8. The gas constituent measuring apparatus according to claim 2,
wherein the first gas is introduced into the cell without mixed with the second gas.

9. The gas constituent measuring apparatus according to claim 1, further comprising:
a presentation device,
wherein the integrated circuit is configured to cause the presentation device to give a predetermined presentation to a user if the humidity inside the cell reaches a value within the predetermined range due to the control performed on the regulator.

10. The gas constituent measuring apparatus according to claim 1, further comprising:
a recording medium,
wherein the integrated circuit is configured to:
if training gas containing one or more constituent gases whose concentrations are already known is drawn into the cell, acquire a third response value output from the gas sensor for the training gas drawn into the cell,
control the regulator on the basis of the result of detection output from the humidity sensor so that the humidity in the cell is within a predetermined range before the training gas is drawn into the cell or after the training gas is discharged from the cell,
acquire a fourth response value output from the gas sensor for the inside of the cell having a humidity controlled through the control performed on the regulator,
record on the recording medium, information regarding a correspondence between the third response value, the fourth response value and the known concentration, and
make the determination on the basis of the first response value, the second response value, and the information.

11. The gas constituent measuring apparatus according to claim 1, further comprising:
a flow rate detector that detects a flow rate of the first gas drawn into the cell; and
a presentation device,
wherein the first gas is exhaled air, and
wherein the integrated circuit is configured to cause the presentation device to give, to a user, a guidance to control a blowing flow rate and a blowing time of the exhaled air based on a result of detection made by the flow rate detector so that the first gas is drawn into the cell at predetermined flow rate for a predetermined period of time.

\* \* \* \* \*